US010877261B2

(12) United States Patent
Tachikawa

(10) Patent No.: US 10,877,261 B2
(45) Date of Patent: Dec. 29, 2020

(54) IMAGE PICKUP APPARATUS, ENDOSCOPE, AND ENDOSCOPE CONTROL METHOD

(71) Applicant: OLYMPUS CORPORATION, Tokyo (JP)

(72) Inventor: Takashi Tachikawa, Aizu-Wakamatsu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/585,016

(22) Filed: Sep. 27, 2019

(65) Prior Publication Data

US 2020/0026059 A1 Jan. 23, 2020

Related U.S. Application Data

(63) Continuation of application No. PCT/JP2017/033837, filed on Sep. 20, 2017.

(30) Foreign Application Priority Data

Mar. 27, 2017 (JP) .................................. 2017-061776

(51) Int. Cl.
*G02B 23/24* (2006.01)
*H04N 5/232* (2006.01)
(Continued)

(52) U.S. Cl.
CPC ....... *G02B 23/243* (2013.01); *G02B 23/2484* (2013.01); *H04N 5/23241* (2013.01); *A61B 1/05* (2013.01); *H04N 2005/2255* (2013.01)

(58) Field of Classification Search
None
See application file for complete search history.

(56) References Cited

U.S. PATENT DOCUMENTS

2012/0050550 A1\* 3/2012 Oba .................... H04N 5/23241
                                                          348/207.99
2013/0265403 A1\* 10/2013 Okawa .................... A61B 1/045
                                                          348/76
(Continued)

FOREIGN PATENT DOCUMENTS

EP       2666401 A1    11/2013
JP    2012-011143 A     1/2012
(Continued)

OTHER PUBLICATIONS

International Search Report dated Dec. 5, 2017 issued in PCT/JP2017/033837.

*Primary Examiner* — Chikaodili E Anyikire
(74) *Attorney, Agent, or Firm* — Scully, Scott, Murphy & Presser, P.C.

(57) ABSTRACT

An image pickup apparatus includes a power supply line, a regulator configured to generate a voltage from a power supply output and output the voltage to a power supply line, a current comparison circuit configured to detect an abnormality of an input current in the regulator, a voltage comparison circuit configured to detect an abnormality of an output voltage in the regulator, a power calculation circuit configured to calculate a power value as a product of the input current and the output voltage, and a power supply line abnormality judgment circuit configured to judge an abnormal state of the power supply line based on the power value, and a power supply control unit configured to control power supply output based on a judgment result of the power supply line abnormality judgment circuit.

1 Claim, 24 Drawing Sheets

(51) Int. Cl.
*A61B 1/05* (2006.01)
*H04N 5/225* (2006.01)

(56) References Cited

U.S. PATENT DOCUMENTS

| | | | |
|---|---|---|---|
| 2016/0220095 A1* | 8/2016 | Shimomura | A61B 1/00029 |
| 2016/0248974 A1* | 8/2016 | Tabuchi | A61B 1/00027 |
| 2016/0262596 A1* | 9/2016 | Ogihara | G02B 23/2484 |
| 2016/0278624 A1* | 9/2016 | Matsumaru | A61B 1/00027 |
| 2019/0239731 A1* | 8/2019 | Hanzawa | A61B 1/0638 |

FOREIGN PATENT DOCUMENTS

| | | |
|---|---|---|
| JP | 2013-027418 A | 2/2013 |
| WO | WO 2013/042647 A1 | 3/2013 |
| WO | WO 2017/065004 A1 | 4/2017 |

\* cited by examiner

FIG. 5

| | | | |
|---|---|---|---|
| FIRST REGULATOR OUTPUT Vol1;ANA | OUTPUT VOLTAGE VALUE (V) | NORMAL TIME [V1] | 3 |
| | | LIMIT TIME [V1_limit] | 4 |
| | OUTPUT CURRENT VALUE (mA) | NORMAL TIME [I1] | 10 |
| | | LIMIT TIME [I1_limit] | 15 |
| SECOND REGULATOR OUTPUT Vol2;I/F | OUTPUT VOLTAGE VALUE (V) | NORMAL TIME [V2] | 2 |
| | | LIMIT TIME [V2_limit] | 2.8 |
| | OUTPUT CURRENT VALUE (mA) | NORMAL TIME [I2] | 2 |
| | | LIMIT TIME [I2_limit] | 5 |
| THIRD REGULATOR OUTPUT Vol3;DIG | OUTPUT VOLTAGE VALUE (V) | NORMAL TIME [V3] | 1 |
| | | LIMIT TIME [V3_limit] | 1.8 |
| | OUTPUT CURRENT VALUE (mA) | NORMAL TIME [I3] | 20 |
| | | LIMIT TIME [I3_limit] | 30 |

FIG. 8

NORMAL TIME (CURRENT)

I3_limit(30mA) ----------------------

I3(20mA) ——————————

I1_limit(15mA) ----------------------

I1(10mA) ——————————

I2_limit(5mA) ----------------------

NORMAL TIME (VOLTAGE)

V1_limit (4V) ----------------------

V1 (3V) ——————————————
V2_limit (2.8V) ----------------------

V2 (2V) ——————————————
V3_limit (1.8V) ----------------------

V3 (1V) ——————————————

0V ——————————————

WHEN SHORT CIRCUIT OCCURS BETWEEN
Vol1 and Vol2 (POWER SUPPLIES)

SHORT CIRCUIT OCCURS
DETECTED BECAUSE POWER EXCEEDS LIMIT,
ALTHOUGH VOLTAGE AND CURRENT DO NOT REACH LIMITS

P1_limit(0.06W)

P1(0.03W)

0W

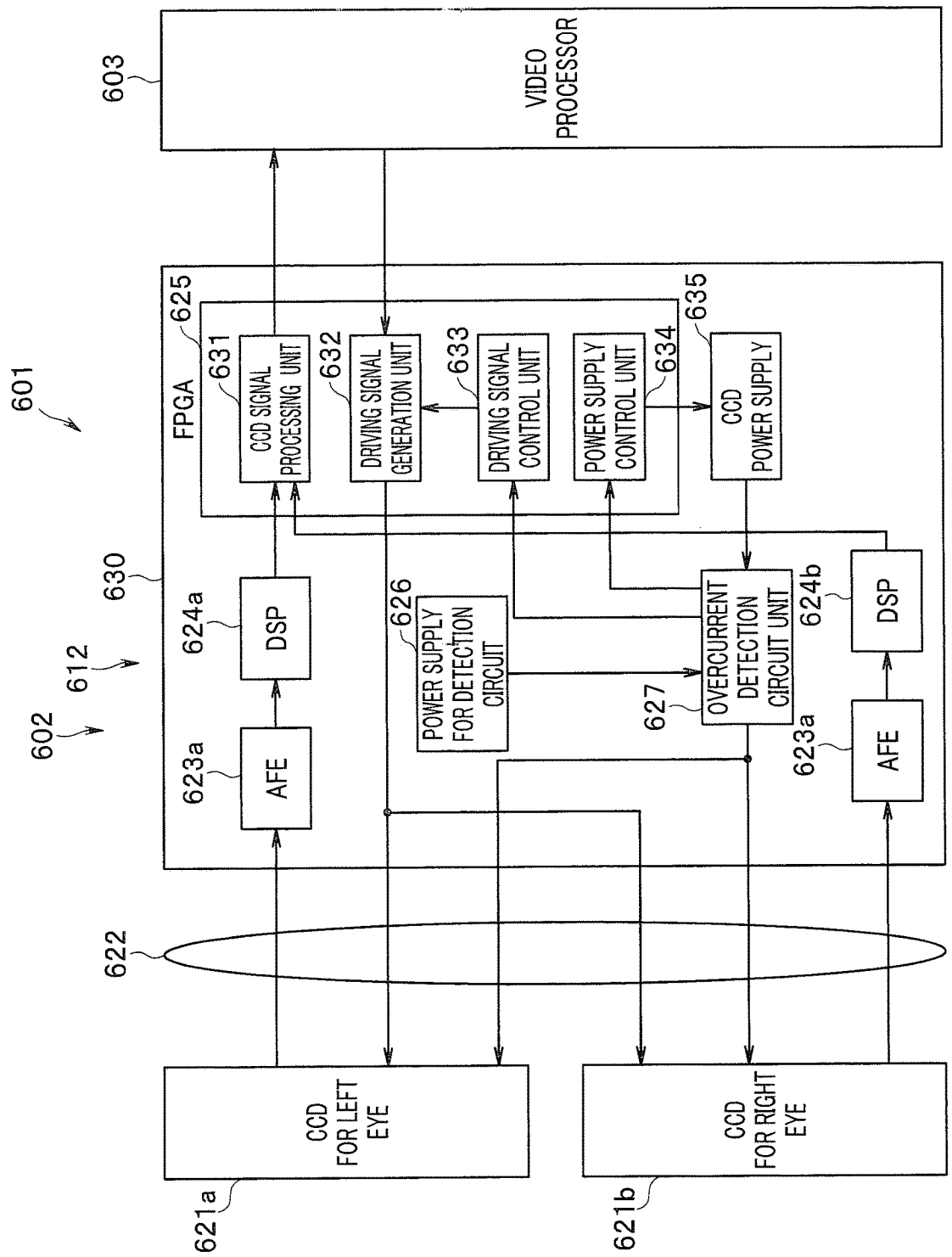

IMAGE PICKUP APPARATUS, ENDOSCOPE, AND ENDOSCOPE CONTROL METHOD

CROSS REFERENCE TO RELATED APPLICATION

This application is a continuation application of PCT/JP2017/033837 filed on Sep. 20, 2017 and claims benefit of Japanese Application No. 2017-061776 filed in Japan on Mar. 27, 2917, the entire contents of which are incorporated herein by this reference.

BACKGROUND OF THE INVENTION

1. Field of the Invention

The present invention relates to an image pickup apparatus, an endoscope, and an endoscope control method, and particularly relates to an image pickup apparatus that includes a solid-state image pickup device and detects an abnormality in a power supply to be supplied to the solid-state image pickup device, an endoscope, and an endoscope control method.

2. Description of the Related Art

An endoscope system including an endoscope that picks up an image of an object within a subject, an image processing apparatus that generates an observation image of the object picked up using the endoscope, and the like has been widely used in a medical field and an industrial field, for example.

As the endoscope in the endoscope system, an endoscope that uses a CMOS image sensor, for example, as a solid-state image pickup device and transmits an image pickup signal to be outputted from the CMOS image sensor to an image processing apparatus in a succeeding stage has been widely known. The above-described CMOS image sensor is generally supplied with predetermined power and driven in response to a predetermined control signal.

For the CMOS image sensor and its peripheral IC (a driving circuit, etc.), heat generation has been a problem as power consumption has increased in recent years. To solve the problem, an image pickup apparatus including a safety circuit configured to monitor a state of a power supply line configured to supply power to an image sensor to prevent the image sensor from generating heat and being damaged has been proposed (Japanese Patent Application Laid-Open Publication No. 2013-27418).

As the safety circuit, a technique for detecting a current value of the power supply line and inputting a detection result to an FPGA disposed in an endoscope connector section to judge a state of an overcurrent while performing error processing, for example, has been known.

In an endoscope including the above-described CMOS image sensor, an example in which a plurality of power supply lines such as an analog power supply line (ANA), an interface power supply line (IF), and a digital power supply line (DIG) are provided in parallel and are wired as the power supply line configured to supply power to the image sensor has been known.

In this type of technique, voltages are respectively supplied from independent regulators to the plurality of power supply lines. More specifically, there has been known an example in which a plurality of power supply lines respectively supplied with voltages from a plurality of regulators, which differ in rated voltage and rated current, such as an analog power supply line (a rated voltage of 3 V and a rated current of 10 mA), an interface power supply line (a rated voltage of 2 V and a rated current of 2 mA), and a digital power supply line (a rated voltage of 1 V and a rated current of 20 mA) are arranged.

On the other hand, in recent years, miniaturization of the endoscope has been increasingly desired, the plurality of power supply lines have been required to be reduced in diameter, and the plurality of power supply lines are disposed in close proximity to one another.

SUMMARY OF THE INVENTION

An image pickup apparatus according to an aspect of the present invention includes an image pickup device, a first power supply line configured to transmit a first voltage to the image pickup device, a second power supply line arranged adjacent to the first power supply line and configured to transmit a second voltage different from the first voltage to the image pickup device, a first regulator configured to generate the first voltage from a power supply output generated in a predetermined power supply and output the first voltage to the first power supply line, a second regulator configured to generate the second voltage from the power supply output and output the second voltage to the second power supply line, a first current detection circuit configured to detect a first current inputted to an input terminal of the first regulator, a first voltage detection circuit configured to detect the first voltage related to a first regulator output outputted from an output terminal of the first regulator, a first power calculation circuit configured to calculate a first power value as a product of a value of the first current detected in the first current detection circuit and a value of the first voltage detected in the first voltage detection circuit, a power supply line abnormality judgment circuit configured to judge an abnormal state related to the first power supply line based on at least the first power value calculated in the first power calculation circuit, and a power supply control circuit configured to control an output of the power supply based on a judgment result in the power supply line abnormality judgment circuit.

An image pickup apparatus according to an aspect of the present invention includes an image pickup device, a first power supply line configured to transmit a first voltage to the image pickup device, a second power supply line arranged adjacent to the first power supply line and configured to transmit a second voltage different from the first voltage to the image pickup device, a first regulator configured to generate the first voltage from a power supply output generated in a predetermined power supply and output the first voltage to the first power supply line, a second regulator configured to generate the second voltage from the power supply output and output the second voltage to the second power supply line, a first current detection circuit configured to detect a first current inputted to an input terminal of the first regulator, a first voltage detection circuit configured to detect the first voltage outputted from an output terminal of the first regulator, a first current comparison circuit configured to output an abnormal signal when an output of the first current detection circuit is a predetermined value or more, a first voltage comparison circuit configured to output an abnormal signal when an output of the first voltage detection circuit deviates from a predetermined range, a power supply line abnormality judgment circuit configured to judge that an abnormality occurs when at least one of the first current comparison circuit and the first voltage comparison circuit outputs an abnormal signal, and a power supply control circuit configured to control an output of the power supply based on a judgment result in the power supply line abnormality judgment circuit.

An endoscope according to an aspect of the present invention includes an insertion section configured to be inserted into a subject, an image pickup device provided at a distal end of the insertion section, a first power supply line configured to transmit a first voltage to the image pickup device, a second power supply line arranged adjacent to the first power supply line and configured to transmit a second voltage different from the first voltage to the image pickup device, a first regulator configured to generate the first voltage from a power supply output generated in a predetermined power supply and output the first voltage to the first power supply line, a second regulator configured to generate the second voltage from the power supply output and output the second voltage to the second power supply line, a first current detection circuit configured to detect a first current inputted to an input terminal of the first regulator, a first voltage detection circuit configured to detect the first voltage outputted from an output terminal of the first regulator, a first current comparison circuit configured to output an abnormal signal when an output of the first current detection circuit is a predetermined value or more, a first voltage comparison circuit configured to output an abnormal signal when an output of the first voltage detection circuit deviates from a predetermined range, a power supply line abnormality judgment circuit configured to acquire a judgment result that an abnormality occurs when at least one of the first current comparison circuit and the first voltage comparison circuit outputs an abnormal signal, and a power supply control circuit configured to control an output of the power supply based on a judgment result acquired by the power supply line abnormality judgment circuit.

An endoscope control method according to an aspect of the present invention is an endoscope control method for controlling an endoscope including an insertion section configured to be inserted into a subject, an image pickup device provided at a distal end of the insertion section, a first power supply line configured to transmit a first voltage to the image pickup device, a second power supply line arranged adjacent to the first power supply line and configured to transmit a second voltage different from the first voltage to the image pickup device, a first regulator configured to generate the first voltage from a power supply output generated in a predetermined power supply and output the first voltage to the first power supply line, and a second regulator configured to generate the second voltage from the power supply output and output the second voltage to the second power supply line, the endoscope control method including detecting a first current inputted to an input terminal of the first regulator using a first current detection circuit, detecting the first voltage outputted from an output terminal of the first regulator using a first voltage detection circuit, outputting an abnormal signal from a first current comparison circuit when an output of the first current detection circuit is a predetermined value or more, outputting an abnormal signal from a first voltage comparison circuit when an output of the first voltage detection circuit deviates from a predetermined range, acquiring a judgment result that an abnormality occurs when at least one of the first current comparison circuit and the first voltage comparison circuit outputs an abnormal signal, and controlling an output of the power supply based on the judgment result.

BRIEF DESCRIPTION OF THE DRAWINGS

FIG. 5 is a table illustrating respective voltage values and current values at a normal time and a limit time of a regulator output related to each of power supply lines in the endoscope according to the first embodiment;

FIG. 8 is a diagram illustrating one setting example of a rated output current and a limit current related to a regulator for each of power supply lines in the endoscope according to the first embodiment;

FIG. 11 is a diagram illustrating one setting example of a rated output voltage and a limit voltage related to a regulator for each of power supply lines in the endoscope according to the first embodiment;

FIG. 24 is a block diagram illustrating a configuration within an FPGA in a stereoscopic endoscope.

DETAILED DESCRIPTION OF THE PREFERRED EMBODIMENT(S)

Embodiments of the present invention will be described below with reference to the drawings.

First Embodiment

Figure 1:
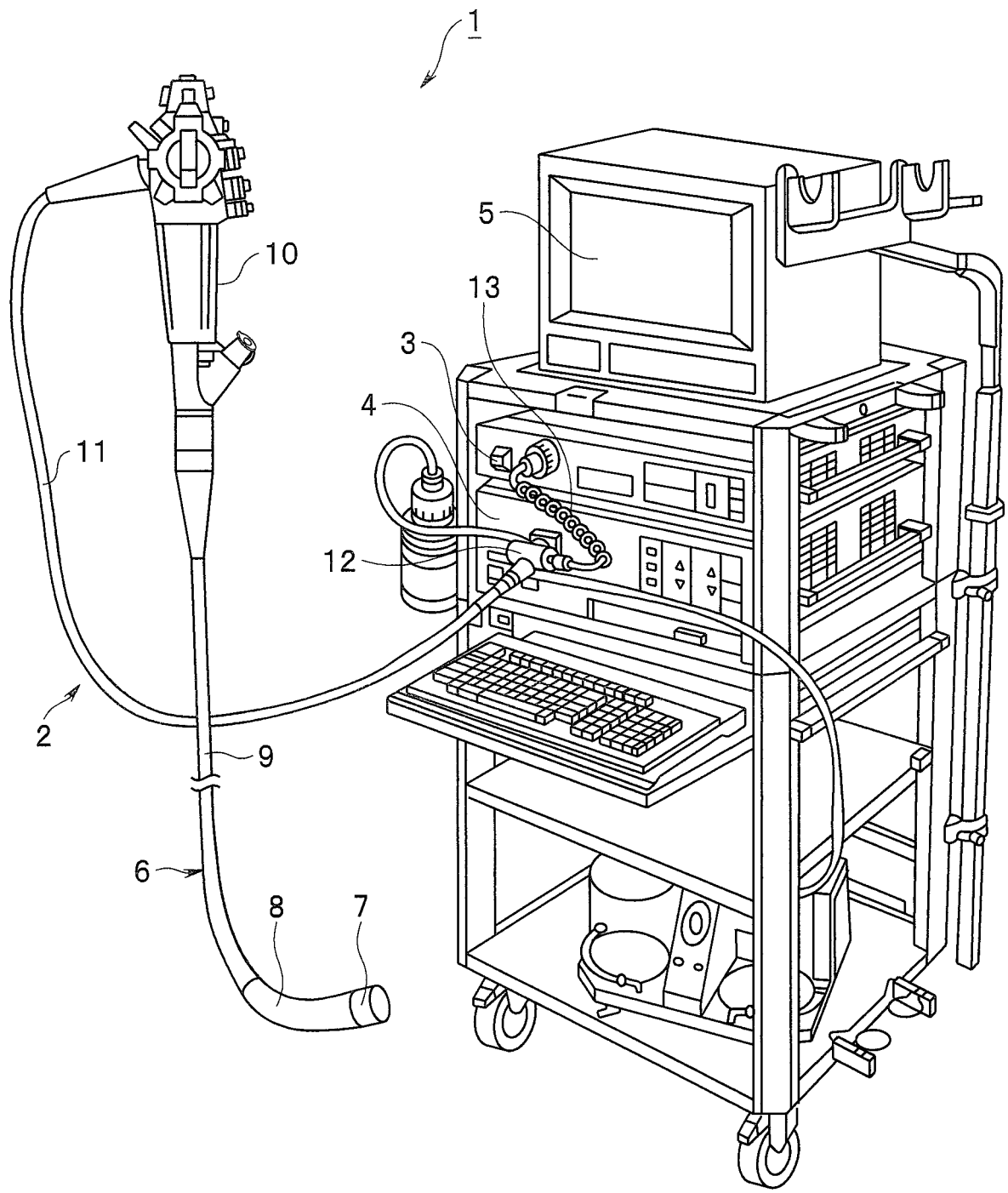
FIG. 1 is a diagram illustrating a configuration of an endoscope system including an endoscope according to a first embodiment of the present invention.
Figure 2:
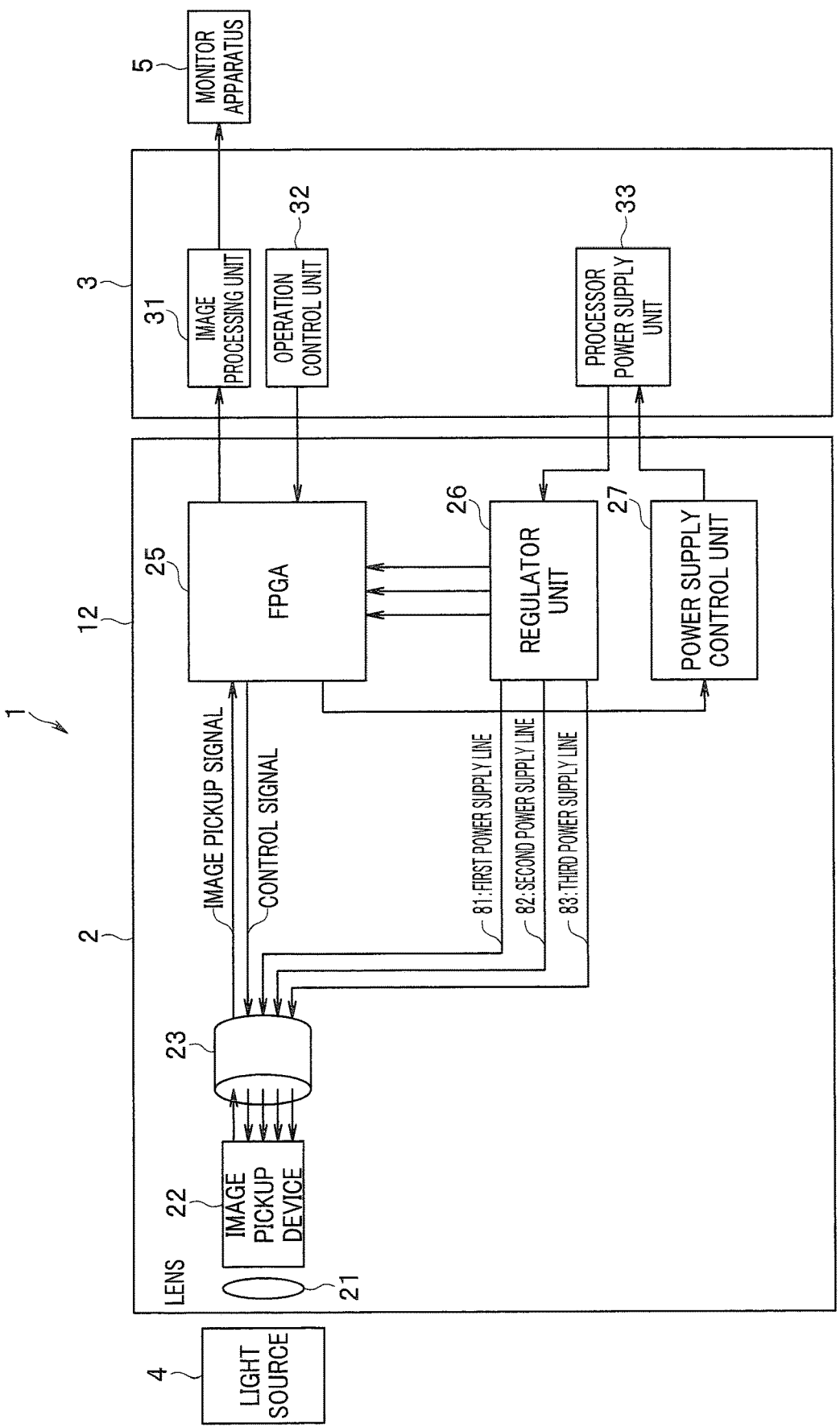
FIG. 2 is a block diagram illustrating an electrical configuration of the endoscope system including the endoscope according to the first embodiment.

FIG. 1 is a diagram illustrating a configuration of an endoscope system including an image pickup apparatus (an endoscope) according to a first embodiment of the present invention, and FIG. 2 is a block diagram illustrating an electrical configuration of the endoscope system including the image pickup apparatus (endoscope) according to the first embodiment.

Note that in the present embodiment, an endoscope that includes a solid-state image pickup device (a CMOS image sensor) and picks up an image of an object within a subject will be described as an example of the image pickup apparatus.

As illustrated in FIGS. 1 and 2, an endoscope system 1 including an image pickup apparatus (an endoscope) according to the first embodiment includes an endoscope 2 configured to observe a subject and pick up an image of the subject, a video processor 3 connected to the endoscope 2 and configured to receive an image pickup signal and subject the image pickup signal to predetermined image processing, a light source apparatus 4 configured to supply illumination light for illuminating the subject, and a monitor apparatus 5 configured to display an observation image corresponding to the image pickup signal.

As illustrated in FIG. 1, the endoscope 2 is configured to include an elongated insertion section 6 configured to be inserted into a body cavity of the subject, for example, an endoscope operation section 10 disposed on a proximal end side of the insertion section 6 and gripped by an operator to perform an operation, and a universal cord 11 having its one end provided to extend from a side portion of the endoscope operation section 10.

The insertion section 6 is configured to include a rigid distal end section 7 provided on a distal end side, a bendable bending section 8 provided at a rear end of the distal end section 7, and a flexible tube section 9 being long and having flexibility provided at a rear end of the bending section 8.

A connector 12 is provided on a proximal end side of the universal cord 11, and the connector 12 is connected to the light source apparatus 4. In other words, a ferrule (not illustrated) as a connection end portion of a fluidic channel protruding from a distal end of the connector 12 and a light guide ferrule (not illustrated) as a supply end of illumination light are detachably connected to the light source apparatus 4.

Further, one end of a connection cable 13 is connected to an electrical contact portion provided on a side surface of the connector 12. The connection cable 13 is internally provided with a signal line configured to transmit an image pickup signal from an image pickup device (a CMOS image sensor) 22 (see FIG. 2) in the endoscope 2, for example, and a connector section at the other end of the connection cable 13 is connected to the video processor 3.

As illustrated in FIG. 2, the endoscope 2 includes an objective optical system 21 including a lens disposed in the distal end section 7 in the insertion section 6 and configured to receive light of an object image and an image pickup device (a CMOS image sensor) 22 disposed on an image forming plane in the objective optical system 21.

The endoscope 2 includes a cable 23 extending from the image pickup device 22 and disposed from the image pickup device 22 to the connector 12 via the insertion section 6, the operation section 10, and the universal cord 11.

Further, the endoscope 2 includes an AFE (not illustrated), an FPGA 25, a regulator unit 26, a power supply control unit 27, and a storage unit (not illustrated) storing specific predetermined ID information in the endoscope 2, and the like that are disposed on a rear end side of the cable 23 and in the connector 12 (see FIG. 2) (the FPGA 25, the regulator unit 26, and the power supply control unit 27, described above, will be described in detail below).

The image pickup device 22 is a solid-state image pickup device composed of a CMOS image sensor in the present embodiment, as described above. The image pickup device 22 photoelectrically converts the object and outputs a predetermined image pickup signal toward a succeeding stage (via the cable 23).

The cable 23 is a cable including a control signal line configured to transmit various types of control signals for driving and controlling the image pickup device 22, a first power supply line 81, a second power supply line 82, and a third power supply line 83 configured to respectively transmit various types of powers to be supplied from the regulator unit 26 including a plurality of regulators, an image pickup signal line configured to transmit an image pickup signal to be outputted from the image pickup device 22, and the like, and is disposed from the image pickup device 22 to the connector 12 in the present embodiment.

The FPGA 25 is composed of a so-called FPGA (field programmable gate array), and is disposed in the connector 12 in the endoscope 2. The FPGA 25 forms a timing adjustment unit configured to perform various types of timing adjustments and transmit a predetermined control signal toward the image pickup device 22 upon receiving operation control from the video processor 3. Further, the FPGA 25 is configured to receive the image pickup signal from the image pickup device 22 and transmit the image pickup signal toward an image processing unit 31 in the video processor 3 in a succeeding stage.

In the present embodiment, in the FPGA 25, various types of comparison circuits configured to judge an abnormality in each of the power supply lines, for example, are formed, which will be described in detail below.

Figure 3:
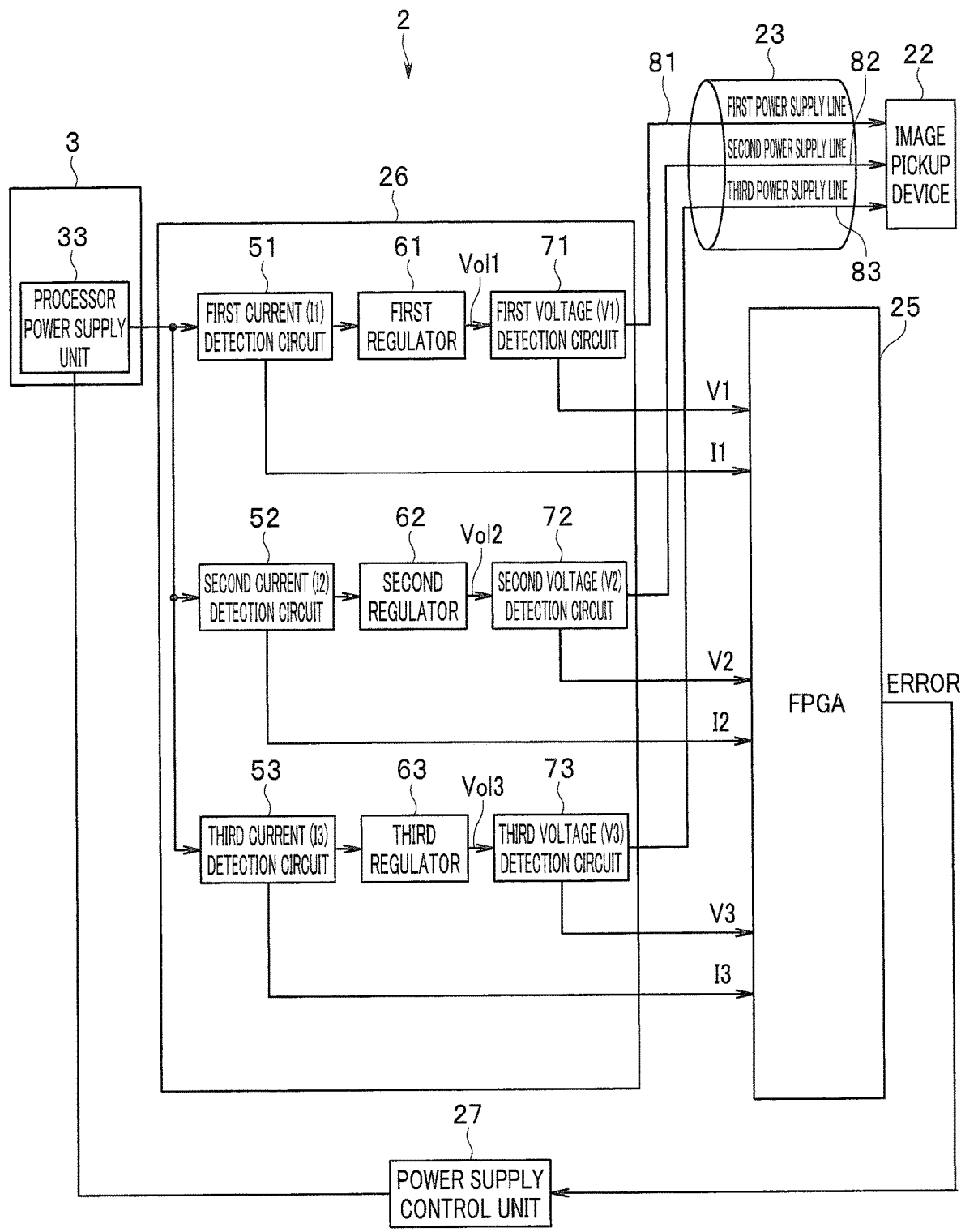
FIG. 3 is a block diagram illustrating a configuration of an FPGA, a regulator unit, a power supply control unit, and a peripheral portion in the endoscope according to the first embodiment.

The regulator unit 26 is configured to include a first regulator 61, a second regulator 62, a third regulator 63, and the like configured to respectively generate and output various types of power supply voltages upon receiving a predetermined power supply voltage from a processor power supply unit 33 in the video processor 3 (see FIG. 3).

In the present embodiment, although details will be described below, the first regulator 61 generates a predetermined first voltage upon receiving the power supply voltage from the processor power supply unit 33 and supplies the predetermined first voltage as a first regulator output to a first power supply line 81.

Similarly, the second regulator 62 generates a second voltage upon receiving the power supply voltage from the processor power supply unit 33 and supplies the second voltage as a second regulator output to a second power supply line 82 in a similar manner as above.

The third regulator 63 generates a third voltage upon receiving the power supply voltage from the processor power supply unit 33 and supplies the third voltage as a third regulator output to the third power supply line 83 in a similar manner as above.

Note that in the present embodiment, an input current and an output voltage of each of the above-described regulators (the first regulator 61, the second regulator 62, and the third regulator 63) in the regulator unit 26 are detected, and respective detection results are transmitted toward various types of comparison circuits in the FPGA 25 (details will be described below).

The power supply control unit 27 receives an error signal from the FPGA 25 while controlling (turning on and off, for example) the processor power supply unit 33 in the video processor 3 in response to the error signal (details will be described below).

The endoscope system 1 according to the present embodiment includes the video processor 3 connected to the endoscope 2 and configured to receive the image pickup signal and subject the image pickup signal to predetermined image processing.

In the present invention, the video processor 3 includes the image processing unit 31 configured to receive the image pickup signal from the endoscope 2, subject the image pickup signal to predetermined image processing, and output the image pickup signal toward the monitor apparatus 5, an operation control unit 32 configured to transmit various types of operation control signals to the endoscope 2, and the processor power supply unit 33 configured to generate a power supply voltage to be supplied to the various types of circuits within the video processor 3 and a power supply voltage to be supplied to each of the above-described regulators (the first regulator 61, the second regulator 62, and the third regulator 63) in the endoscope 2.

<Configuration of FPGA 25, Regulator Unit 26, Power Supply Control Unit 27, and Power Supply Lines>

Then, a configuration of the FPGA 25, the regulator unit 26, the power supply control unit 27, and the power supply lines in the present embodiment will be described in detail with reference to FIGS. 3, 4, and 5 in addition to FIG. 2.

Figure 4:
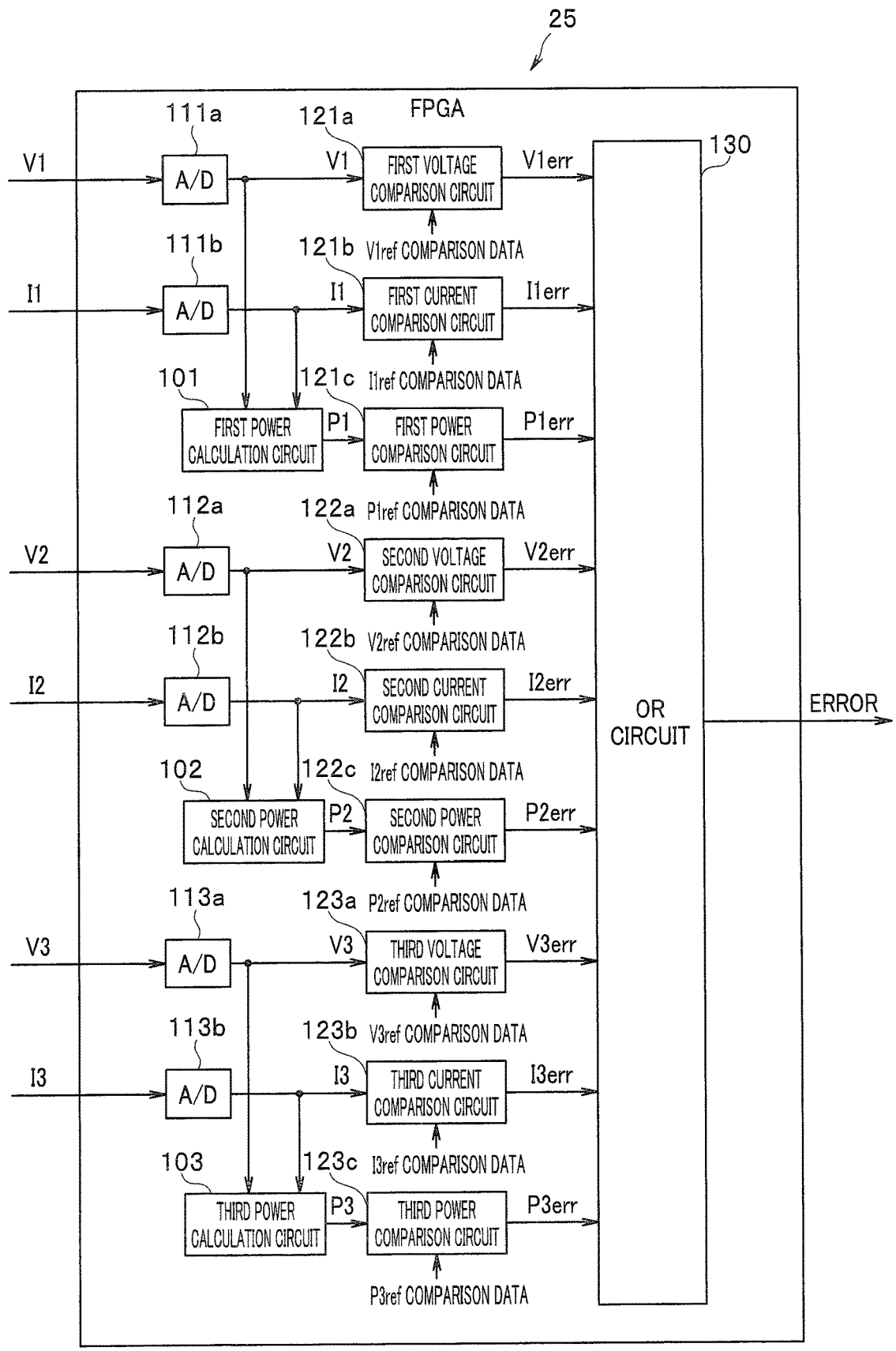
FIG. 4 is a block diagram illustrating a configuration within the FPGA in the endoscope according to the first embodiment.

FIG. 3 is a block diagram illustrating a configuration of the FPGA, the regulator unit, the power supply control unit, the power supply lines, and a peripheral portion in the endoscope according to the first embodiment, and FIG. 4 is a block diagram illustrating a configuration within the FPGA in the endoscope according to the first embodiment. FIG. 5 is a table illustrating respective voltage values and current values at a normal time and a limit time of a regulator output related to each of the power supply lines in the endoscope according to the first embodiment.

<Regulator Unit 26>

First, a configuration within the regulator unit 26 will be described with reference to FIG. 3.

As illustrated in FIG. 3, the regulator unit 26 includes the first regulator 61, the second regulator 62, and the third regulator 63 configured to each receive a predetermined power supply voltage from the processor power supply unit 33 in the video processor 3 and respectively generate and output various types of power supply voltages (V1, V2, and V3) for driving the image pickup device 22, as described above.

The first regulator 61 generates the predetermined first voltage V1 upon receiving the power supply voltage from the processor power supply unit 33 and supplies the predetermined first voltage V1 as a first regulator output Vol1 toward the image pickup device 22 via the first power supply line 81.

The first regulator 61 functions as a first regulator configured to generate the first voltage from a power supply output generated in the predetermined power supply unit (the processor power supply unit 33) and output the first voltage as a first regulator output.

In the present embodiment, a voltage (3 V) for an analog power supply (ANA) is assumed as the first voltage V1. As illustrated in FIG. 5, the following are assumed as the first regulator output Vol1:

First rated voltage [V1]=3 V
First limit voltage [V1_limit]=4 V
First rated current [I1]=10 mA
First limit current [I1_limit]=15 mA Similarly, the second regulator 62 generates the predetermined second voltage V2 upon receiving the power supply voltage from the processor power supply unit 33 and supplies the predetermined second voltage V2 as a second regulator output Vol2 toward the image pickup device 22 via the second power supply line 82 in a similar manner as above.

The second regulator 62 functions as a second regulator configured to generate the second voltage from a power supply output generated in the predetermined power supply unit (the processor power supply unit 33) and output the second voltage as a second regulator output.

In the present embodiment, a voltage (2 V) for an interface power supply (IF) is assumed as the second voltage V2. As illustrated in FIG. 5, the following are assumed as the second regulator output Vol2:

Second rated voltage [V2]=2 V
Second limit voltage [V2_limit]=2.8 V
Second rated current [I2]=2 mA
Second limit current [I2_limit]=5 mA The third regulator 63 generates the predetermined third voltage V3 upon receiving the power supply voltage from the processor power supply unit 33 and supplies the predetermined third voltage V3 as a third regulator output Vol3 toward the image pickup device 22 via the third power supply line 83 in a similar manner as above.

The third regulator 63 functions as a third regulator configured to generate the third voltage from a power supply output generated in the predetermined power supply unit (the processor power supply unit 33) and output the third voltage as a third regulator output.

In the present embodiment, a voltage (1 V) for a digital power supply (DIG) is assumed as the third voltage V3. As illustrated in FIG. 5, the following are assumed as the third regulator output Vol3:

Third rated voltage [V3]=1 V
Third limit voltage [V3_limit]=1.8 V
Third rated current [I3]=20 mA
Third limit current [I2_limit]=30 mA On the other hand, the regulator unit 26 includes a first current detection circuit 51 configured to detect a first current (I1) to be inputted to an input terminal of the first regulator 61 and a first voltage detection circuit 71 configured to detect a first voltage (V1) related to the first regulator output Vol1 to be outputted from an output terminal of the first regulator 61.

The first current detection circuit 51 functions as a first current detection circuit configured to detect the first current to be inputted to the input terminal of the first regulator, and the first voltage detection circuit 71 functions as a first voltage detection circuit configured to detect the first voltage related to the first regulator output to be outputted from the output terminal of the first regulator.

The first voltage (V1) detected in the first voltage detection circuit 71 is inputted to a predetermined first voltage value AD converter 111a in the FPGA 25, and the first current (I1) detected in the first current detection circuit 51 is inputted to a predetermined first current value AD converter 111b in the FPGA 25 (see FIG. 4).

The regulator unit 26 includes a second current detection circuit 52 configured to detect a second current (I2) to be inputted to an input terminal of the second regulator 62 and a second voltage detection circuit 72 configured to detect a second voltage (V2) related to the second regulator output Vol2 to be outputted from an output terminal of the second regulator 62.

The second current detection circuit 52 functions as a second current detection circuit configured to detect the second current to be inputted to the input terminal of the second regulator, and the second voltage detection circuit 72 functions as a second voltage detection circuit configured to detect the second voltage related to the second regulator output to be outputted from the output terminal of the second regulator.

The second voltage (V2) detected in the second voltage detection circuit 72 is inputted to a predetermined second voltage value AD converter 112a in the FPGA 25, and the second current (I2) detected in the second current detection circuit 52 is inputted to a predetermined second current value AD converter 112b in the FPGA 25 (see FIG. 4).

Further, the regulator unit 26 includes a third current detection circuit 53 configured to detect a third current (I3) to be inputted to an input terminal of the third regulator 63 and a third voltage detection circuit 73 configured to detect a third voltage (V3) related to the third regulator output Vol3 to be outputted from an output terminal of the third regulator 63.

The third current detection circuit 53 functions as a third current detection circuit configured to detect the third current to be inputted to the input terminal of the third regulator, and the third voltage detection circuit 73 functions as a third voltage detection circuit configured to detect the third voltage related to the third regulator output to be outputted from the output terminal of the third regulator.

The third voltage (V3) detected in the third voltage detection circuit 73 is inputted to a predetermined third voltage value AD converter 113a in the FPGA 25, and the third current (I3) detected in the third current detection circuit 53 is inputted to a predetermined third current value AD converter 113b in the FPGA 25 (see FIG. 4).

<Power Supply Lines 81, 82, and 83>

The first power supply line 81 is an analog power supply line connected to the first regulator 61 via the first voltage detection circuit 71 and configured to transmit the first regulator output Vol1 toward the image pickup device 22.

The first power supply line 81 functions as a first power supply line connected to the first regulator and configured to transmit the first regulator output to be outputted from the first regulator.

The second power supply line 82 is an interface power supply line wired adjacent to the first power supply line 81 within the cable 23, connected to the second regulator 62 via the second voltage detection circuit 72, and configured to transmit the second regulator output Vol2 toward the image pickup device 22.

The second power supply line 82 is a power supply line wired adjacent to the first power supply line and functions as a second power supply line connected to the second regulator 62 and configured to transmit the second regulator output to be outputted from the second regulator.

Further, the third power supply line 83 is a power supply line wired adjacent to the first power supply line 81 and the second power supply line 82, and is a digital power supply line connected to the third regulator 63 via the third voltage detection circuit 73 and configured to transmit the third regulator output Vol3 toward the image pickup device 22.

The third power supply line 83 is a power supply line wired adjacent to the first power supply line and the second power supply line, and functions as a third power supply line connected to the third regulator and configured to transmit the third regulator output to be outputted from the third regulator.

<FPGA 25>

Then, the FPGA 25 will be described with reference to FIG. 4. FIG. 4 is a block diagram illustrating the configuration within the FPGA in the endoscope according to the first embodiment.

The FPGA 25 is composed of a so-called FPGA (field programmable gate array) and is disposed in the above-described connector 12 in the endoscope 2, as described above (see FIG. 2). The FPGA 25 transmits various types of control signals toward the image pickup device 22 while receiving an image pickup signal from the image pickup device 22 and transmitting the image pickup signal to the image processing unit 31 upon receiving operation control from the video processor 3.

In the present embodiment, in the FPGA 25, an AD converter configured to judge an abnormality in each of the power supply lines, various types of comparison circuits, and the like are formed. The AD converter, the comparison circuits, and their peripheral circuits will be described below.

<AD Converter>

As illustrated in FIG. 4, the FPGA 25 includes the first voltage value AD converter 111a configured to receive the first voltage V1 detected in the first voltage detection circuit 71 and subject the first voltage V1 to predetermined AD conversion, the first current value AD converter 111b configured to receive the first current I1 detected in the first current detection circuit 51 and subject the first current I1 to predetermined AD conversion, the second voltage value AD converter 112a configured to receive the second voltage V2 detected in the second voltage detection circuit 72 and subject the second voltage V2 to predetermined AD conversion, the second current value AD converter 112b configured to receive the second current I2 detected in the second current detection circuit 52 and subject the second current I2 to predetermined AD conversion, the third voltage value AD converter 113a configured to receive the third voltage V3 detected in the third voltage detection circuit 73 and subject the third voltage V3 to predetermined AD conversion, and the third current value AD converter 113b configured to receive the third current I3 detected in the third current detection circuit 53 and subject the third current I3 to predetermined AD conversion.

<First Voltage Comparison Circuit and First Current Comparison Circuit>

The FPGA 25 includes a first voltage comparison circuit 121a connected to an output end of the first voltage value AD converter 111a and configured to compare the first voltage V1 with predetermined first voltage comparison data V1ref and output a comparison result, and a first current comparison circuit 121b connected to an output end of the first current value AD converter 111b and configured to compare the first current I1 with predetermined first current comparison data I1ref and output a comparison result.

The first voltage comparison circuit 121a receives the first voltage V1 outputted from the first voltage value AD converter 111a and compares the first voltage V1 with the predetermined first voltage comparison data V1ref, and outputs an error signal first voltage error signal V1err when the first voltage exceeds the first voltage comparison data V1ref.

The first current comparison circuit 121b receives the first current I1 outputted from the first current value AD converter 111b and compares the first current I1 with the predetermined first current comparison data I1ref, and outputs an error signal first current error signal I1err when the first current exceeds the first current comparison data I1ref.

<Second Voltage Comparison Circuit and Second Current Comparison Circuit>

Further, the FPGA 25 includes a second voltage comparison circuit 122a connected to an output end of the second voltage value AD converter 112a and configured to compare the second voltage V2 with predetermined second voltage comparison data V2ref and output a comparison result, and a second current comparison circuit 122b connected to an output end of the second current value AD converter 112b and configured to compare the second current I2 with predetermined second current comparison data I2ref and output a comparison result.

The second voltage comparison circuit 122a receives the second voltage V2 outputted from the second voltage value AD converter 112a and compares the second voltage V2 with the predetermined second voltage comparison data V2ref, and outputs an error signal second voltage error signal V2err when the second voltage exceeds the second voltage comparison data V2ref.

The second current comparison circuit 122b receives the second current I2 outputted from the second current value AD converter 112b and compares the second current I2 with the predetermined second current comparison data I2ref, and outputs an error signal second current error signal I2err when the second current exceeds the second current comparison data I2ref.

<Third Voltage Comparison Circuit and Third Current Comparison Circuit>

Further, the FPGA 25 includes a third voltage comparison circuit 123a connected to an output end of the third voltage value AD converter 113a and configured to compare the third voltage V3 with predetermined third voltage comparison data V3ref and output a comparison result, and a third current comparison circuit 123b connected to an output end of the third current value AD converter 113b and configured to compare the third current I3 with predetermined third current comparison data I3ref and output a comparison result.

The third voltage comparison circuit 123a receives the third voltage V3 outputted from the third voltage value AD converter 113a and compares the third voltage V3 with the predetermined third voltage comparison data V3ref, and outputs an error signal third voltage error signal V3err when the third voltage exceeds the third voltage comparison data V3ref.

The third current comparison circuit 123b receives the third current I3 outputted from the third current value AD converter 113b and compares the third current I3 with the predetermined third current comparison data I3ref, and outputs an error signal third current error signal I3err when the third current exceeds the third current comparison data I3ref.

<First to Third Voltage Comparison Data>

Note that in the present embodiment, the first voltage comparison data V1ref, the second voltage comparison data V2ref, and the third voltage comparison data V3ref are respectively set to limit voltage values in the first regulator output Vo1, the second regulator output Vo2, and the third regulator output Vo3 to be outputted from the first regulator 61, the second regulator 62, and the third regulator 63 (see FIG. 5).

In other words, the following are set:
First voltage comparison data V1ref=first limit voltage [V1_limit]=4 V
Second voltage comparison data V2ref=second limit voltage [V2_limit]=2.8 V
Third voltage comparison data V3ref=third limit voltage [V3_limit]=1.8 V <First to Third Circuit Comparison Data>

Similarly, in the present embodiment, the first current comparison data I1ref, the second current comparison data I2ref, and the third current comparison data I3ref are respectively set to limit current values in the first regulator output Vo1, the second regulator output Vo2, and the third regulator output Vo3 to be outputted from the first regulator 61, the second regulator 62, and the third regulator 63 (see FIG. 5).

In other words, the following are set:
First current comparison data I1ref=first limit current [I1_limit]=15 mA
Second current comparison data I2ref=second limit current [I2_limit]=5 mA
Third current comparison data I3ref=third limit current [I3_limit]=30 mA <First to Third Power Calculation Circuits>

The FPGA 25 includes a first power calculation circuit 101 configured to receive an output of the first voltage value AD converter 111a (i.e., a value of the first voltage V1 detected in the first voltage detection circuit 71) and an output of the first current value AD converter 111b (i.e., a value of the first current I1 detected in the first current detection circuit 51) and calculate a product of the value of the first voltage V1 and the value of the first current I1, that is, a power value of the first regulator output Vo1 (a first output power P1) to be outputted from the first regulator 61.

The first power calculation circuit 101 functions as a first power calculation circuit configured to calculate a first power value as the product of the value of the first current detected in the first current detection circuit and the value of the first voltage detected in the first voltage detection circuit.

Further, the FPGA 25 includes a second power calculation circuit 102 configured to receive an output of the second voltage value AD converter 112a (i.e., a value of the second voltage V2 detected in the second voltage detection circuit 72) and an output of the second current value AD converter 112b (i.e., a value of the second current I2 detected in the second current detection circuit 52) and calculate a product of the value of the second voltage V2 and the value of the second current I2, that is, a power value of the second regulator output Vol2 (a second output power P2) to be outputted from the second regulator 62.

The second power calculation circuit 102 functions as a second power calculation circuit configured to calculate a second power value as the product of the value of the second current detected in the second current detection circuit and the value of the second voltage detected in the second voltage detection circuit.

Further, the FPGA 25 includes a third power calculation circuit 103 configured to receive an output of the third voltage value AD converter 113a (i.e., a value of the third voltage V3 detected in the third voltage detection circuit 73) and an output of the third current value AD converter 113b (i.e., a value of the third current I3 detected in the third current detection circuit 53) and calculate a product of the value of the third voltage V3 and the value of the third current I3, that is, a power value of the third regulator output Vol3 (a third output power P3) to be outputted from the third regulator 63.

The third power calculation circuit 103 functions as a third power calculation circuit configured to calculate a third power value as the product of the value of the third current detected in the third current detection circuit and the value of the third voltage detected in the third voltage detection circuit.

<First to Third Power Comparison Circuits and First to Third Power Comparison Data>

On the other hand, the FPGA 25 includes a first power comparison circuit 121c connected to an output end of the first power calculation circuit 101 and configured to compare the first output power P1 with predetermined first power comparison data P1ref and output a comparison result.

The FPGA 25 includes a second power comparison circuit 122c connected to an output end of the second power calculation circuit 102 and configured to compare the second output power P2 with predetermined second power comparison data P2ref and output a comparison result.

Further, the FPGA 25 includes a third power comparison circuit 123c connected to an output end of the third power calculation circuit 103 and configured to compare the third output power P3 with predetermined third power comparison data P3ref and output a comparison result.

The first power comparison circuit 121c receives the first output power P1 outputted from the first power calculation circuit 101 and compares the first output power P1 with the predetermined first power comparison data P1ref, and outputs an error signal first power error signal P1err when the first output power P1 exceeds the first power comparison data P1ref.

The first power comparison circuit 121c functions as a power supply line abnormality judgment unit configured to judge an abnormal state related to the first power supply line based on at least the first power value calculated in the first power calculation circuit.

The second power comparison circuit 122c receives the second output power P2 outputted from the second power calculation circuit 102 and compares the second output power P2 with the predetermined second power comparison data P2ref, and outputs an error signal second power error signal P2err when the second output power P2 exceeds the second power comparison data P2ref.

Further, the third power comparison circuit 123c receives the third output power P3 outputted from the third power calculation circuit 103 and compares the third output power P3 with the predetermined third power comparison data P3ref, and outputs an error signal third power error signal P3err when the third output power P3 exceeds the third power comparison data P3ref.

Note that in the present embodiment, the first power comparison data P1ref, the second power comparison data P2ref, and the third power comparison data P3ref are respectively set to limit power values in the first regulator output Vol1, the second regulator output Vol2, and the third regulator output Vol3 to be outputted from the first regulator 61, the second regulator 62, and the third regulator 63 (see FIG. 5).

For example, the following are set:

First power comparison data P1ref=first limit power value [P1_limit]=0.06 w

Second power comparison data P2ref=second limit power value [P2_limit]=0.014 W

Third power comparison data P3ref=third limit power value [P3_limit]=0.054 W

Although set to the limit power value (the first limit power value [P1_limit]) in the first regulator output Vol1 to be outputted from the first regulator 61 in the present embodiment, as described below, the first power comparison data P1ref is more specifically set to a value corresponding to a power value obtained when it is assumed that a short circuit has occurred between a live wire side of the first power supply line 81 and a live wire side of the second power supply line 82.

<OR Circuit 130>

On the other hand, the FPGA 25 includes an OR circuit 130 connected to respective output ends of the first voltage comparison circuit 121a, the first current comparison circuit 121b, the first power comparison circuit 121c, the second voltage comparison circuit 122a, the second current comparison circuit 122b, the second power comparison circuit 122c, the third voltage comparison circuit 123a, the third current comparison circuit 123b, and the third power comparison circuit 123c.

The OR circuit 130 receives the comparison result from each of the above-described comparison circuits, that is, each of the above-described error signals, and outputs a predetermined error signal ERROR toward the power supply control unit 27 when the OR circuit 130 has received the error signal.

The OR circuit 130 and each of the above-described comparison circuits (particularly, the power comparison circuit such as the first power comparison circuit 121c) function as a power supply line abnormality judgment unit configured to judge an abnormal state related to the power supply line such as the first power supply line 81 based on the power value calculated in the power calculation circuit such as the first power calculation circuit 101.

<Power Supply Control Unit 27>

The power supply control unit 27 receives the above-described error signal ERROR from the FPGA 25 while controlling the processor power supply unit 33 in the video processor 3 in response to the error signal ERROR. In other words, the power supply control unit 27 receives the error signal ERROR based on a result processed in the various types of comparison circuits in the FPGA 25, and transmits a control signal for performing control (e.g., on/off control) of the processor power supply unit 33 toward the video processor 3 in response to the error signal ERROR.

The power supply control unit 27 functions as a power supply control unit configured to control an output of the power supply unit (the processor power supply unit 33) based on a judgment result in the power supply line abnormality judgment unit.

<Function of Present Embodiment>

Then, a function of the endoscope according to the first embodiment will be described below with reference to FIG. 6.

Figure 6:
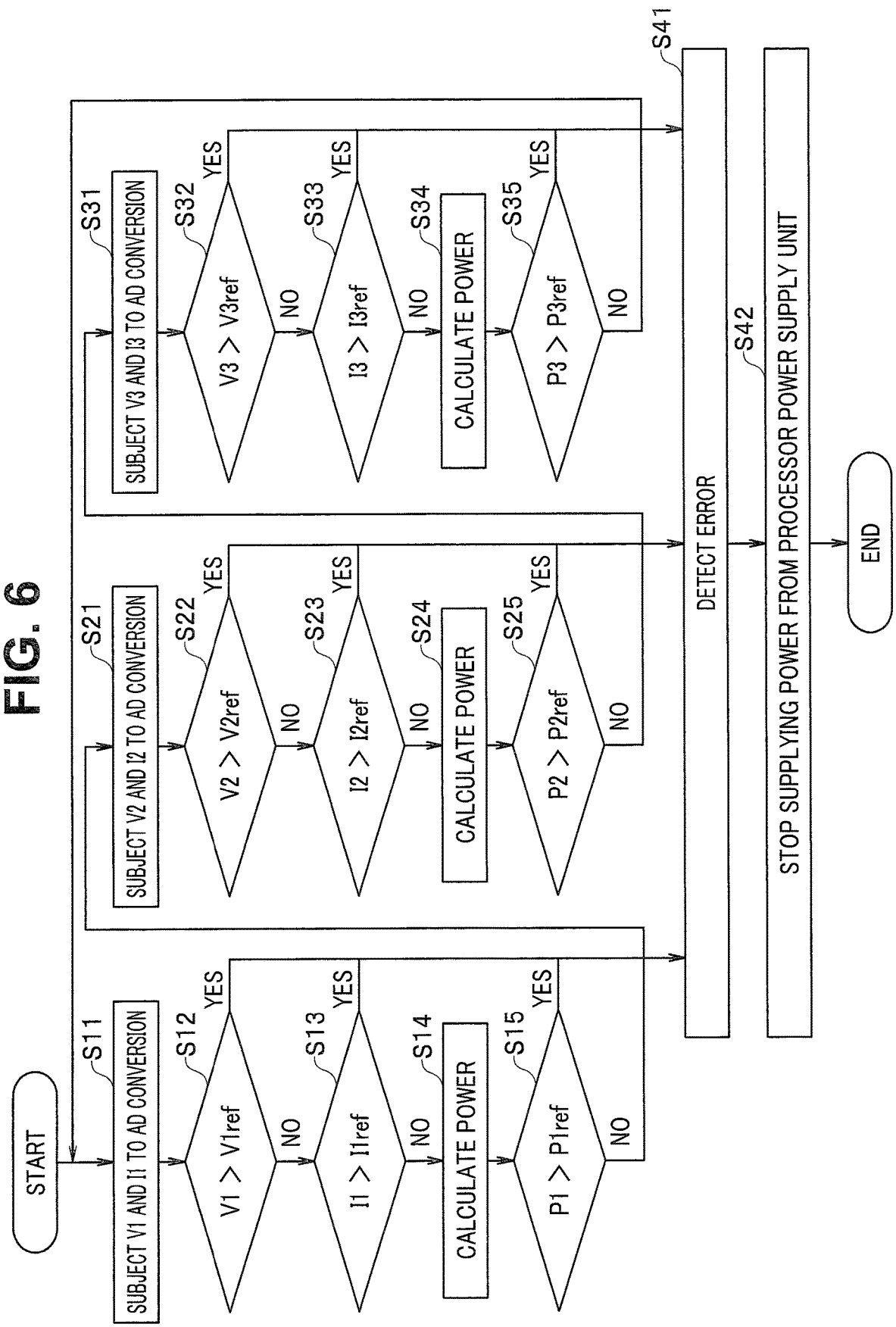
FIG. 6 is a flowchart illustrating an error detecting function associated with a regulator output voltage, an output current, and power consumption related to each of power supply lines in the endoscope according to the first embodiment.

FIG. 6 is a flowchart illustrating an error detecting function associated with a regulator output voltage, an output current, and power consumption related to each of the power supply lines in the endoscope according to the first embodiment.

In the present embodiment, the first regulator 61, the second regulator 62, and the third regulator 63 respectively generate the first voltage V1, the second voltage V2, and the third voltage V3 based on the power supply voltage outputted from the processor power supply unit 33 in the video processor 3 and output the first voltage V1, the second voltage V2, and the third voltage V3 as the first regulator output Vol1, the second regulator output Vol2, and the third regulator output Vol3.

Then, the first voltage value AD converter 111a and the first current value AD converter 111b in the FPGA 25 respectively subject the first voltage V1 and the first current I1 to AD conversion and output the first voltage V1 and the first current I1 (step S11).

Then, the first voltage comparison circuit 121a compares the first voltage V1 outputted from the first voltage value AD converter 111a with the first voltage comparison data V1ref. More specifically, the first voltage comparison circuit 121a compares the first voltage V1 with the first limit voltage V1_limit=4 V. The processing proceeds to step S41 after the first voltage comparison circuit 121a outputs the first voltage error signal V1err if the first voltage V1 exceeds the first limit voltage V1_limit=4 V, and the processing proceeds to step S13 if the first voltage V1 does not exceed the first limit voltage V1_limit=4 V (step S12).

Then, the first current comparison circuit 121b compares the first current I1 outputted from the first current value AD converter 111b with the first current comparison data I1ref. More specifically, the first current comparison circuit 121b compares the first current I1 with the first limit current I1_limit=15 mA. The processing proceeds to step S41 after the first current comparison circuit 121b outputs the first current error signal I1err if the first current I1 exceeds the first limit current I1_limit=15 mA, and the processing proceeds to step S14 if the first current I1 does not exceed the first limit current I1_limit=15 mA (step S13).

Then, the first power calculation circuit 101 receives the output of the first voltage value AD converter 111a (i.e., the value of the first voltage V1 detected in the first voltage detection circuit 71) and the output of the first current value AD converter 111b (i.e., the value of the first current I1 detected in the first current detection circuit 51) and calculates the product of the value of the first voltage V1 and the value of the first current I1, that is, the power value of the first regulator output Vol1 (the first output power P1) to be outputted from the first regulator 61 (step S14).

Then, the first power comparison circuit 121c compares the first power P1 outputted from the first power calculation circuit 101 with the first power comparison data P1ref. More specifically, the first power comparison circuit 121c compares the first power P1 with the first limit power P1_limit=0.06 W. The processing proceeds to step S41 after the first power comparison circuit 121c outputs the first power error signal P1err if the first power P1 exceeds the first limit power P1_limit=0.06 W, and the processing proceeds to step S21 if the first power P1 does not exceed the first limit power P1_limit=0.06 W (step S15).

Then, the second voltage value AD converter 112a and the second current value AD converter 112b in the FPGA 25 respectively subject the second voltage V2 and the second current I2 to AD conversion and output the second voltage V2 and the second current I2 (step S21).

Then, the second voltage comparison circuit 122a compares the second voltage V2 outputted from the second voltage value AD converter 112a with the second voltage comparison data V2ref. More specifically, the second voltage comparison circuit 122a compares the second voltage V2 with the second limit voltage V2_limit=2.8 V. The processing proceeds to step S41 after the second voltage comparison circuit 122a outputs the second voltage error signal V2err if the second voltage V2 exceeds the second limit voltage V2_limit=2.8 V, and the processing proceeds to step S23 if the second voltage V2 does not exceed the second limit voltage V2_limit=2.8 V (step S22).

Then, the second current comparison circuit 122b compares the second current I2 outputted from the second current value AD converter 112b with the second current comparison data I2ref. More specifically, the second current comparison circuit 122b compares the second current I2 with the second limit current I2_limit=5 mA. The processing proceeds to step S41 after the second current comparison circuit 122b outputs the second current error signal I2err if the second current I2 exceeds the second limit current I2_limit=5 mA, and the processing proceeds to step S24 if the second current I2 does not exceed the second limit current I2_limit=5 mA (step S23).

Then, the second power calculation circuit 102 receives the output of the second voltage value AD converter 112a (i.e., the value of the second voltage V2 detected in the second voltage detection circuit 72) and the output of the second current value AD converter 112b (i.e., the value of the second current I2 detected in the second current detection circuit 52), and calculates the product of the value of the second voltage V2 and the value of the second current I2, that is, the power value of the second regulator output Vol2 (the second output power P2) to be outputted from the second regulator 62 (step S24).

Then, the second power comparison circuit 122c compares the second power P2 outputted from the second power calculation circuit 102 with the second power comparison data P2ref. More specifically, the second power comparison circuit 122c compares the second power P2 with the second limit power P2_limit=0.014 W. The processing proceeds to step S41 after the second power comparison circuit 122c outputs the second power error signal P2err if the second power P2 exceeds the second limit power P2_limit=0.014 W, and the processing proceeds to step S31 if the second power P2 does not exceed the second limit power P2_limit=0.014 W (step S25).

Then, the third voltage value AD converter 113a and the third current value AD converter 113b in the FPGA 25 respectively subject the third voltage V3 and the third current I3 to AD conversion and output the third voltage V3 and the third current I3 (step S31).

Then, the third voltage comparison circuit 123a compares the third voltage V3 outputted from the third voltage value AD converter 113a with the third voltage comparison data V3ref. More specifically, the third voltage comparison circuit 123a compares the third voltage V3 with the third limit voltage V3_limit=1.8 V. The processing proceeds to step S41 after the third voltage comparison circuit 123a outputs the third voltage error signal V3err if the third voltage V3 exceeds the third limit voltage V3_limit=1.8 V, and the processing proceeds to step S33 if the third voltage V3 does not exceed the third limit voltage V3_limit=1.8 V (step S32).

Then, the third current comparison circuit 123b compares the third current I3 outputted from the third current value AD converter 113b with the third current comparison data I3ref. More specifically, the third current comparison circuit 123b compares the third current I3 with the third limit current I3_limit=30 mA. The processing proceeds to step S41 after the third current comparison circuit 123b outputs the third current error signal I3err if the third current I3 exceeds the third limit current I3_limit=30 mA, and the processing proceeds to step S34 if the third current I3 does not exceed the third limit current I3_limit=30 mA (step S33).

Then, the third power calculation circuit 103 receives the output of the third voltage value AD converter 113a (i.e., the value of the third voltage V3 detected in the third voltage detection circuit 73) and the output of the third current value AD converter 113b (i.e., the value of the third current I3 detected in the third current detection circuit 53), and calculates the product of the value of the third voltage V3 and the value of the third current I3, that is, the power value of the third regulator output Vo3 (the third output power P3) to be outputted from the third regulator 63 (step S34).

Then, the third power comparison circuit 123c compares the third power P3 outputted from the third power calculation circuit 103 with the third power comparison data P3ref. More specifically, the third power comparison circuit 123c compares the third power P3 with the third limit power P3_limit=0.054 W. The processing proceeds to step S41 after the third power comparison circuit 123c outputs the third power error signal P3err if the third power P3 exceeds the third limit power P3_limit=0.054 W, and the processing returns to step S11 if the third power P3 does not exceed the third limit power P3_limit=0.054 W (step S35).

Accordingly, each of the above-described comparison circuits such as the first voltage comparison circuit 121a, the first current comparison circuit 121b, the first power comparison circuit 121c, the second voltage comparison circuit 122a, the second current comparison circuit 122b, the second power comparison circuit 122c, the third voltage comparison circuit 123a, the third current comparison circuit 123b, and the third power comparison circuit 123c transmits, if the inputted voltage value (V1, V2, V3), current value (I1, I2, I3), or power value (P1, P2, P3) exceeds the corresponding comparison data, described above, the error signal, as described above.

The OR circuit 130 outputs, when it receives any one of the error signals, the error signal ERROR toward the power supply control unit 27, assuming that a malfunction such as a short circuit has occurred in a corresponding portion of the first power supply line 81, the second power supply line 82, or the third power supply line 83 (step S41).

Figure 7:
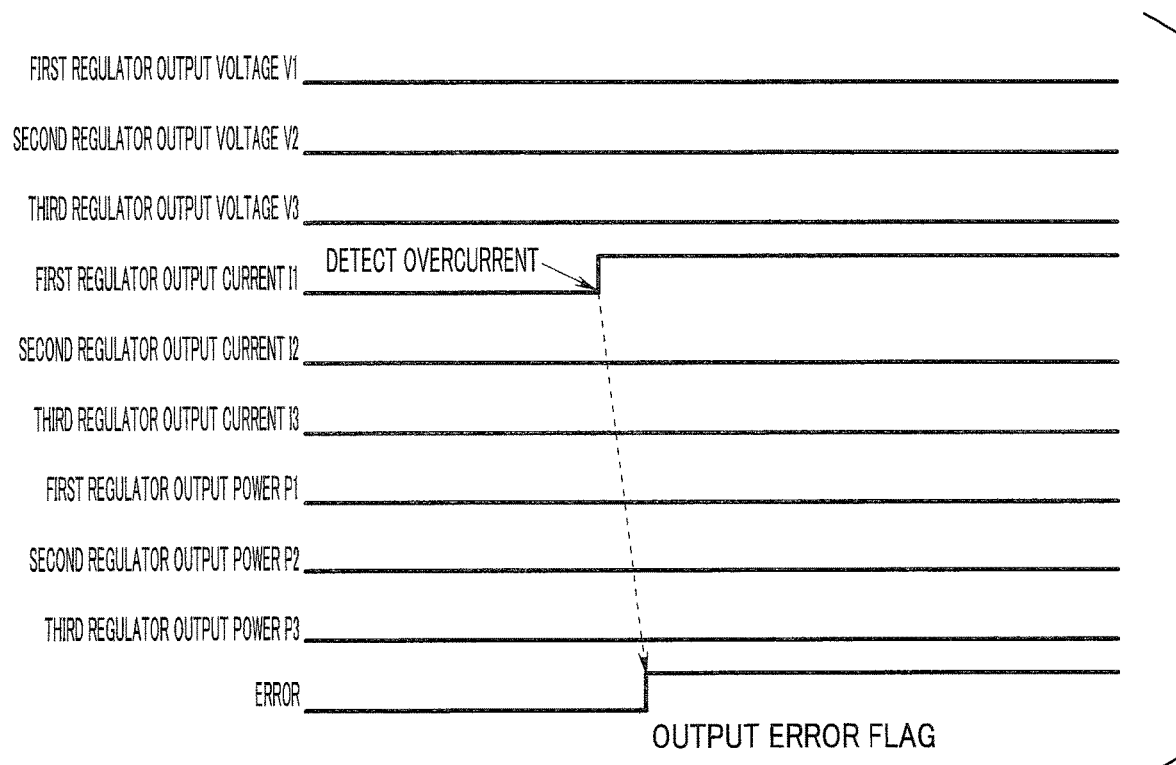
FIG. 7 is a timing chart illustrating how error detection is performed when overcurrent detection is performed in the endoscope according to the first embodiment.

FIG. 7 is a timing chart illustrating how error detection is performed when overcurrent detection is performed in the endoscope according to the first embodiment.

More specifically, if the first current I1 related to the first regulator 61 exceeds the first current comparison data I1ref (the first limit current I1_limit) in the first current comparison circuit 121b, that is, if an overcurrent is detected in the first power supply line 81, as illustrated in FIG. 7, for example, the first current error signal I1err is transmitted toward the OR circuit 130 from the first current comparison circuit 121b (step S13 described above).

The OR circuit 130 outputs the error signal ERROR toward the power supply control unit 27 upon receiving the first current error signal I1err (step S41).

Then, the power supply control unit 27 transmits a control signal to the processor power supply unit 33 in the video processor 3 upon receiving the error signal ERROR from the OR circuit 130, and stops supplying power to each of the regulators (the first regulator 61, the second regulator 62, and the third regulator 63) from the processor power supply unit 33 (step S42).

<Specific Function and Effect of Present Embodiment>

Then, a more specific function and effect of the endoscope according to the first embodiment will be described with reference to FIGS. 8 to 14.

Figure 9:
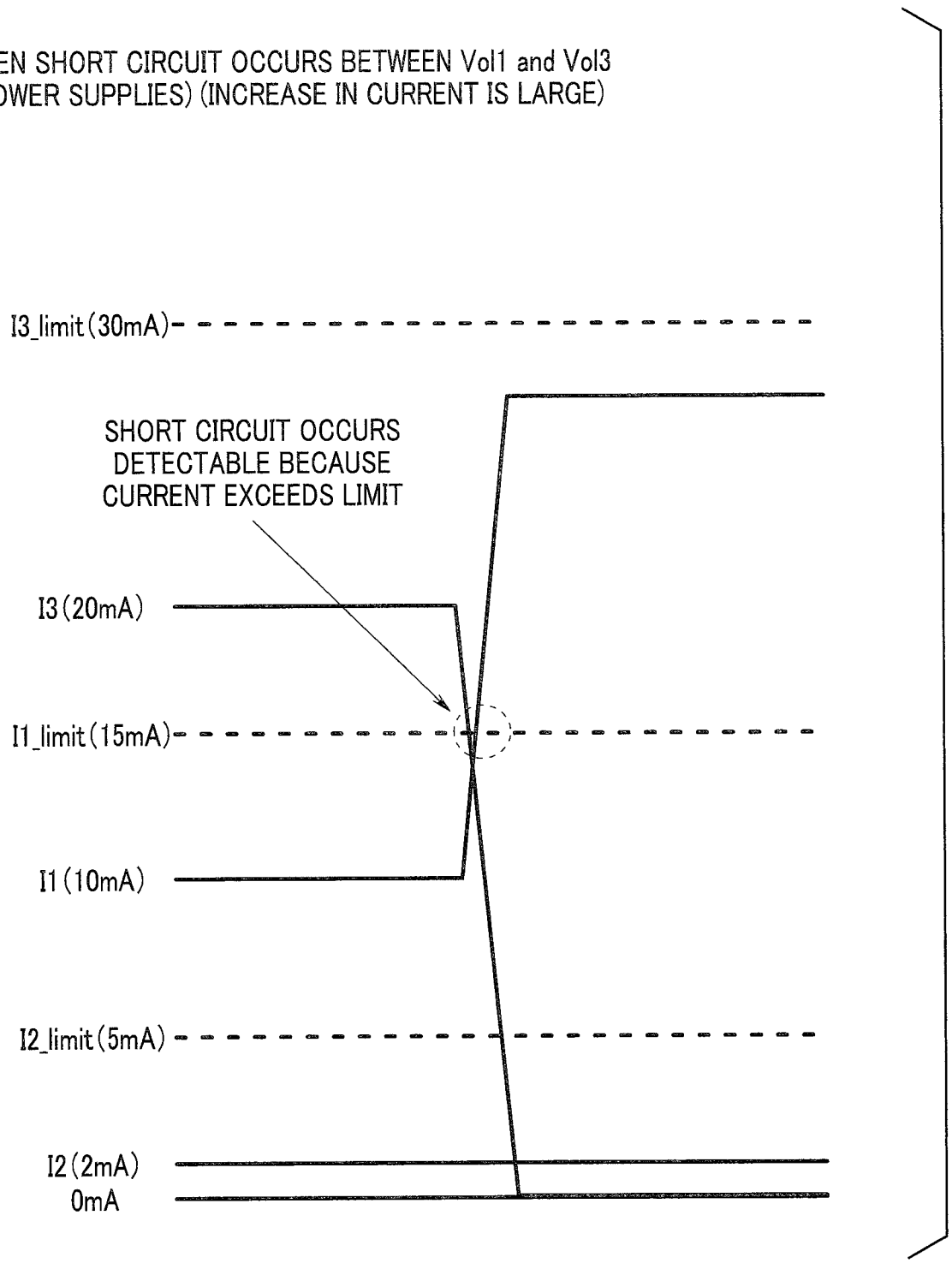
FIG. 9 is a diagram illustrating a relationship between an output current and a limit current in each of an analog power supply line and a digital power supply line when a short circuit occurs between the power supply lines in the endoscope according to the first embodiment.
Figure 10:
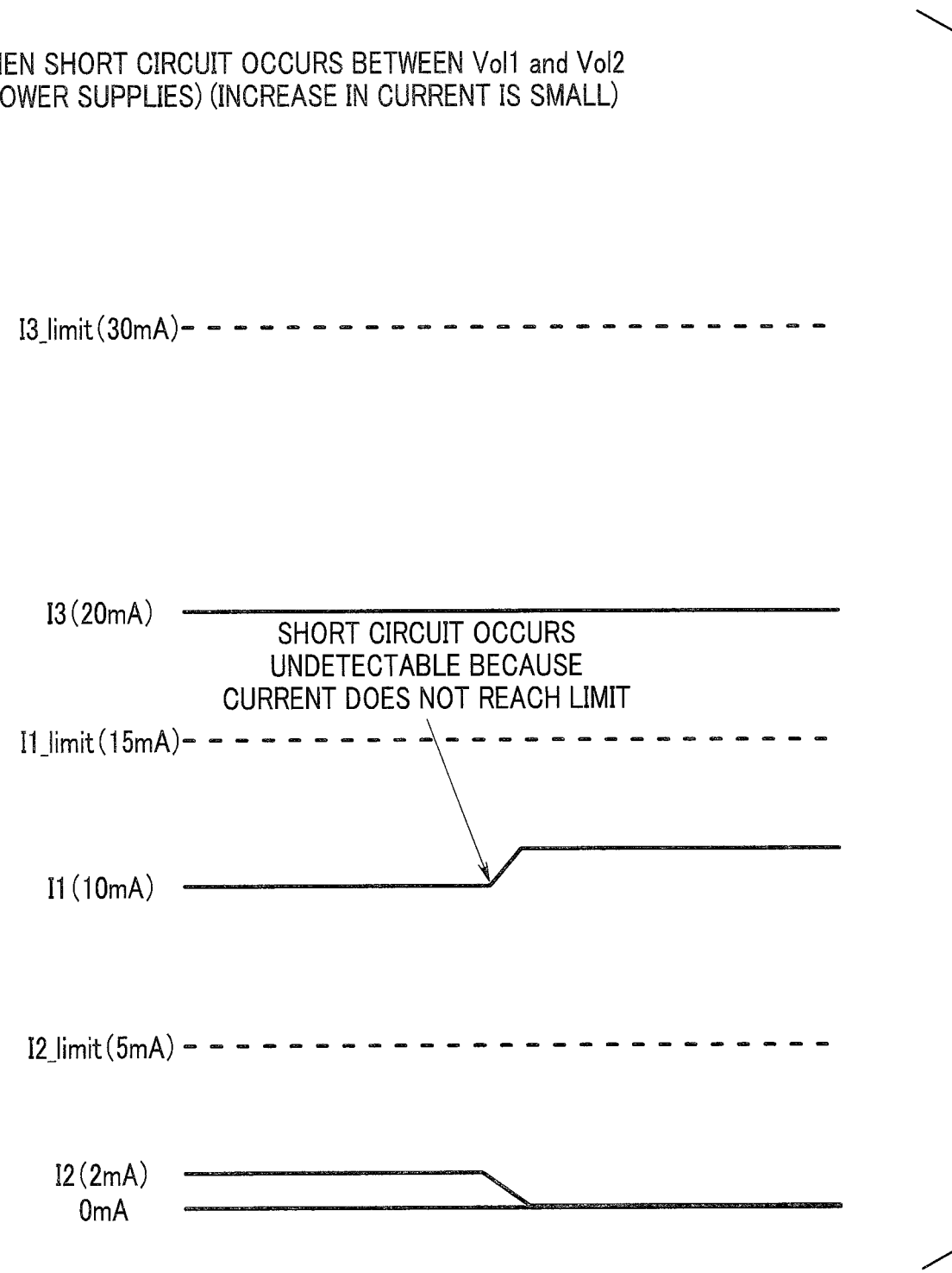
FIG. 10 is a diagram illustrating a relationship between an output current and a limit current in each of an analog power supply line and an interface power supply line when a short circuit occurs between the power supply lines in the endoscope according to the first embodiment.

FIG. 8 is a diagram illustrating one setting example of a rated output current and a limit current related to a regulator for each of power supply lines in the endoscope according to the first embodiment, FIG. 9 is a diagram illustrating a relationship between an output current and a limit current in each of an analog power supply line and a digital power supply line when a short circuit has occurred between the power supply lines in the endoscope according to the first embodiment, and FIG. 10 is a diagram illustrating a relationship between an output current and a limit current in each of an analog power supply line and an interface power supply line when a short circuit has occurred between the power supply lines in the endoscope according to the first embodiment.

Figure 12:
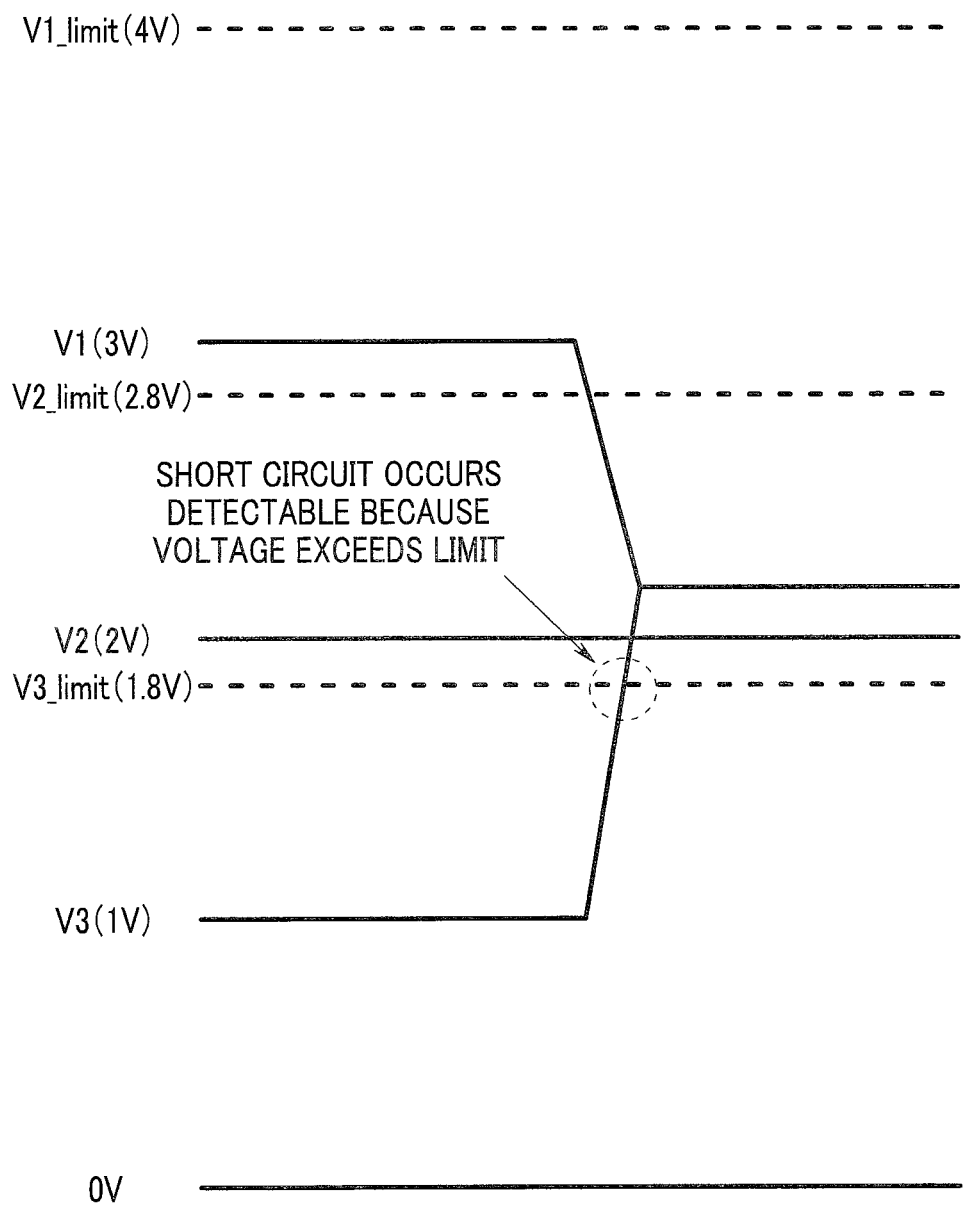
FIG. 12 is a diagram illustrating a relationship between an output voltage and a limit voltage in each of an analog power supply line and a digital power supply line when a short circuit occurs between the power supply lines in the endoscope according to the first embodiment.
Figure 13:
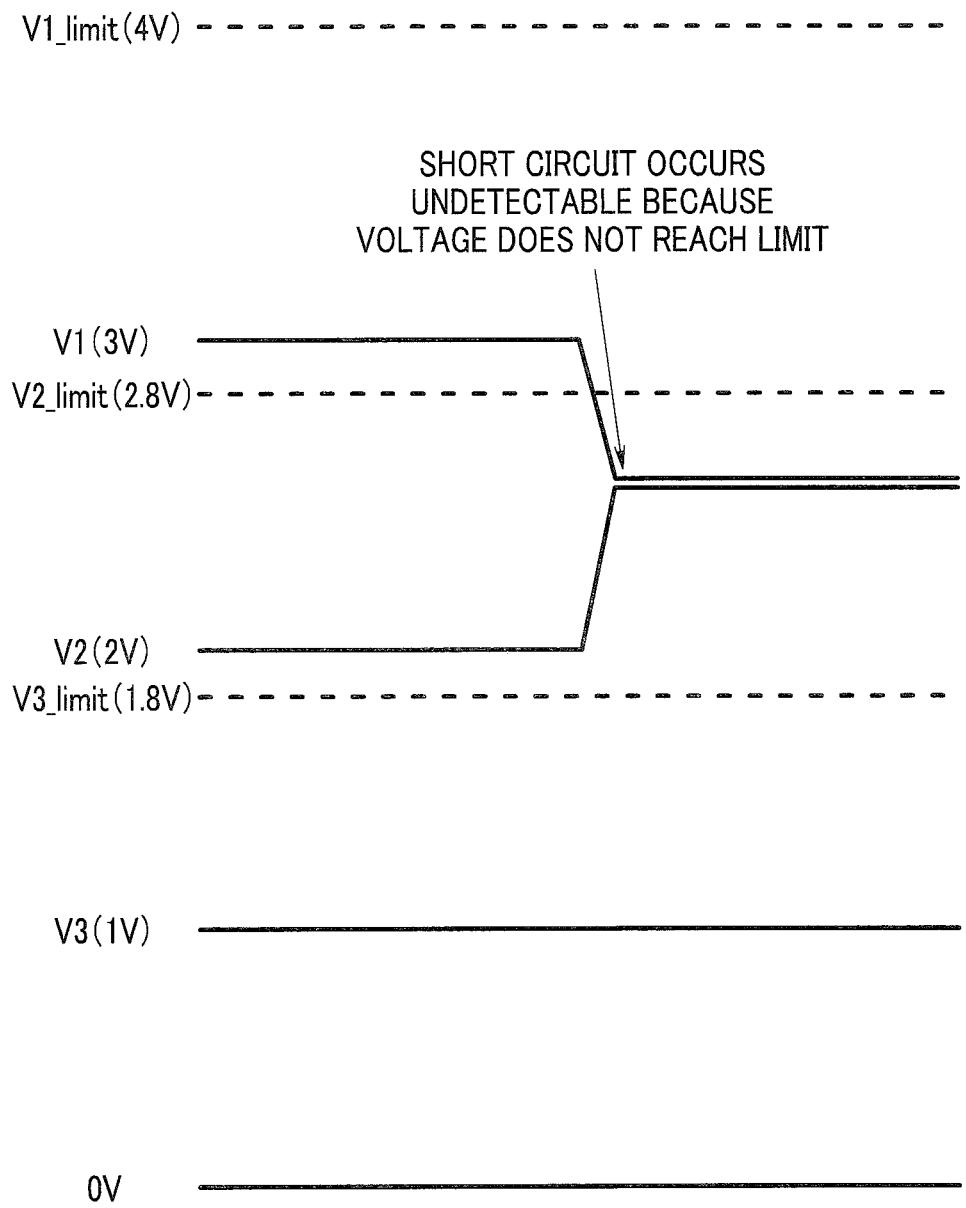
FIG. 13 is a diagram illustrating a relationship between an output voltage and a limit voltage in each of an analog power supply line and an interface power supply line when a short circuit occurs between the power supply lines in the endoscope according to the first embodiment.

FIG. 11 is a diagram illustrating one setting example of a rated output voltage and a limit voltage related to a regulator for each of power supply lines in the endoscope according to the first embodiment, FIG. 12 is a diagram illustrating a relationship between an output voltage and a limit voltage in each of an analog power supply line and a digital power supply line when a short circuit has occurred between the power supply lines in the endoscope according to the first embodiment, and FIG. 13 is a diagram illustrating a relationship between an output voltage and a limit voltage in each of an analog power supply line and an interface power supply line when a short circuit has occurred between the power supply lines in the endoscope according to the first embodiment.

Figure 14:
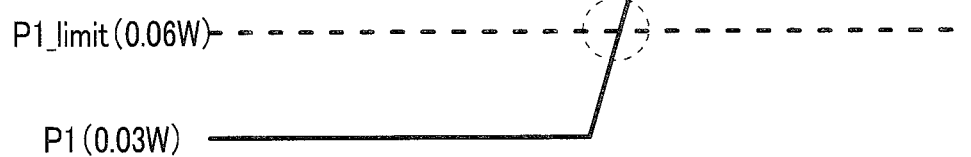
FIG. 14 is a diagram illustrating a relationship between an output power and a limit power in an analog power supply line when a short circuit occurs between the analog power supply line and an interface power supply line in the endoscope according to the first embodiment.

FIG. 14 is a diagram illustrating a relationship between an output power and a limit power in an analog power supply line when a short circuit has occurred between the analog power supply line and an interface power supply line in the endoscope according to the first embodiment.

As described above, in the present embodiment, the following are assumed:
First rated voltage [V1]=3 V
First limit voltage [V1_limit]=4 V
First rated current [I1]=10 mA
First limit current [I1_limit]=15 mA
Second rated voltage [V2]=2 V
Second limit voltage [V2_limit]=2.8 V
Second rated current [I2]=2 mA
Second limit current [I2_limit]=5 mA
Third rated voltage [V3]=1 V
Third limit voltage [V3_limit]=1.8 V
Third rated current [I3]=20 mA
Third limit current [I3_limit]=30 mA <State of Each Power Supply Line at Normal Time>

In the endoscope according to the present embodiment, a first regulator output Vo1 (an analog power supply ANA) having a first rated voltage [V1]=3 V and a first rated current

[I1]=10 mA is outputted from the first regulator 61 and is supplied to the first power supply line 81 (an analog power supply line) at a normal time.

A second regulator output Vol2 (an interface power supply IF) having a second rated voltage [V2]=2 V and a second rated current [I2]=2 mA is outputted from the second regulator 62 and is supplied to the second power supply line 82 (an interface power supply line).

Further, a third regulator output Vol3 (a digital power supply DIG) having a third rated voltage [V3]=1 V and a third rated current [I3]=20 mA is outputted from the third regulator 63 and is supplied to the third power supply line 83 (a digital power supply line).

In other words, as illustrated in FIGS. 8 and 11, the regulator outputs respectively having "the first rated voltage [V1]=3 V and the first rated current [I1]=10 mA", "the second rated voltage [V2]=2 V and the second rated current [I2]=2 mA", "the third rated voltage [V3]=1 V and the third rated current [I3]=20 mA" are respectively supplied to the first power supply line 81, the second power supply line 82, and the third power supply line 83 at the normal time.

A first limit current [I1_limit]=15 mA, a second limit current [I2_limit]=5 mA, and a third limit current [I3_limit]= 30 mA are added to FIG. 8, and a first limit voltage [V1_limit]=4 V, a second limit voltage [V2_limit] =2.8 V, and a third limit voltage [V3_limit]=1.8 V are added to FIG. 11.

<Functions and Effects of Voltage Comparison Circuit and Current Comparison Circuit>

Then, in the endoscope according to the present embodiment, respective functions and effects of each of the voltage comparison circuits and each of the current comparison circuits will be described while referring to a state where a short circuit has occurred between the live wire side of the first power supply line 81 and the live wire side of the third power supply line 83.

<Case Where Short Circuit Has Occurred Between First Power Supply Line 81 and Third Power Supply Line 83>

As described above, in the endoscope according to the present embodiment, the plurality of various types of power supply lines, described above, are provided in parallel and wired within the cable 23 in the endoscope 2. The plurality of power supply lines have been disposed in closer proximity to one another by a recent request for a reduction in diameter. Therefore, under such a situation, a more appropriate safety measure has been required for a short circuit between the respective live wires of the adjacent power supply lines.

In the endoscope according to the present embodiment, it is assumed that a short circuit or a state closer to the short circuit has occurred between the respective live wire sides of the first power supply line 81 (the analog power supply line: a rated voltage of 3 V and a rated current of 10 mA) and the third power supply line 83 (the digital power supply line: a rated voltage of 1 V and a rated current of 20 mA).

Note that the short circuit between the live wire side of the first power supply line 81 and the live wire side of the third power supply line 83 can be said to be a situation where a degree of increase in current between the power supply lines due to the short circuit is relatively large and can be said to be a situation where a potential difference between both the power supply lines is relatively large.

At this time, when a current in each of the power supply lines is paid attention to, the third current I3 (20 mA) to be outputted from the regulator (the third regulator 63) for the third power supply line 83 (the digital power supply line) rapidly decreases to be approximately 0 mA, as illustrated in FIG. 9.

On the other hand, the first current I1 (10 mA) to be outputted from the regulator (the first regulator 61) for the first power supply line 81 (the analog power supply line) rapidly increases because the first current I1 also flows into a load of the third power supply line 83 (the digital power supply line), and the output current (the first current I1) of the first regulator 61 may exceed the first limit current I1_limit (15 mA).

If the output current (the first current I1) from the first regulator 61 exceeds the first limit current I1_limit (15 mA), that is, the first current I1 exceeds the first current comparison data I1_ref, the first current error signal I1_err is outputted from the first current comparison circuit 121b (in step S13 described above; see FIG. 6). Therefore, the error signal ERROR is outputted from the OR circuit 130, and supply of power from the processor power supply unit 33 is stopped under the control of the power supply control unit 27 (step S42 described above).

Accordingly, in the present embodiment, in the situation where the degree of increase in current is relatively large, for example, the short circuit between the first power supply line 81 (the analog power supply line; a rated voltage of 3 V and a rated current of 10 mA) and the third power supply line 83 (the digital power supply line; a rated voltage of 1 V and a rated current of 20 mA), an abnormal state of each of the power supply lines can be detected using an overcurrent detecting function.

On the other hand, when a voltage to be supplied to each of the power supply lines is paid attention to, as illustrated in FIG. 12, the first voltage V1 (a rated voltage of 3 V) to be outputted from the first regulator 61 for the first power supply line 81 (the analog power supply line) decreases, while the third voltage V3 (a rated voltage of 1 V) to be outputted from the third regulator 63 for the third power supply line 83 (the digital power supply line) increases, and the output voltage (the third voltage V3) of the third regulator 63 may exceed the third limit voltage V3_limit=1.8 V.

If the output voltage (the third voltage V3) of the third regulator 63 exceeds the third limit voltage V3_limit (1.8 V), that is, if the third voltage V3 exceeds the third voltage comparison data V3ref, the third voltage error signal V3err is outputted from the third voltage comparison circuit 123a (step S32 described above; see FIG. 6). Therefore, the error signal ERROR is outputted from the OR circuit 130, and supply of power from the processor power supply unit 33 is stopped under the control of the power supply control unit 27 (step S42 described above).

Accordingly, in the present embodiment, in the situation where the potential difference between both the power supply lines is relatively large, for example, the short circuit between the first power supply line 81 (the analog power supply line; a rated voltage of 3 V and a rated current of 10 mA) and the third power supply line 83 (the digital power supply line; a rated voltage of 1 V and a rated current of 20 mA), an abnormal state of each of the power supply lines can be detected without using the above-described overcurrent detecting function.

<Case Where Short Circuit Has Occurred Between First Power Supply Line 81 and Second Power Supply Line 82>

Then, it is assumed that a short circuit or a state close to the short circuit has occurred between the respective live wire sides of the first power supply line 81 (the analog power supply line; a rated voltage of 3 V and a rated current of 10 mA) and the second power supply line 82 (the interface power supply line; a rated voltage of 2 V and a rated current of 2 m).

Note that the short circuit between the live wire side of the first power supply line 81 and the live wire side of the second power supply line 82 can be said to be a situation where a degree of increase in current between the power supply lines due to the short circuit is a relatively small and can be said to be a situation where a potential difference between both the power supply lines is relatively small.

At this time when a current in each of the power supply lines is paid attention to, the second current I2 (2 mA) to be outputted from the regulator (the second regulator 62) for the second power supply line 82 (the interface power supply line) decreases to be approximately 0 mA, as illustrated in FIG. 10.

On the other hand, although the first current I1 (10 mA) to be outputted from the regulator (the first regulator 61) for the first power supply line 81 (the analog power supply line) increases because the first current I1 also flows into a load of the second power supply line 82 (the interface power supply line), the degree of increase in current is small because the load of the interface power supply line is not so large, and the output current (the first current I1) of the first regulator 61 need not necessarily exceed the first limit current (15 mA).

In this case, if the output current (the first current I1) of the first regulator 61 does not exceed the first limit current I1_limit (15 mA), an abnormal state cannot be detected using the overcurrent detecting function, that is, the first current error signal I1err is not outputted from the first current comparison circuit 121b. Therefore, the abnormal state may be difficult to detect regardless of the short circuit having occurred between the respective live wires of the first power supply line 81 and the second power supply line 82.

In the present embodiment, not only a current abnormality but also a voltage abnormality from the regulator is detected, as described above. For a case where the potential difference between both the power supply lines is relatively large, like in the example illustrated in FIG. 12, described above, the abnormal state of each of the power supply lines can be detected without using the above-described overcurrent detecting function. However, if the potential difference is relatively small, the abnormal state may be unable to be detected.

In other words, although the first voltage V1 (a rated voltage of 3 V) to be outputted from the first regulator 61 for the first power supply line 81 (the analog power supply line) decreases, and the second voltage V2 (a rated voltage of 2 V) to be outputted from the second regulator 62 for the second power supply line 82 (the interface power supply line) increases so that the first voltage V1 and the second voltage V2 have substantially the same potential, as illustrated in FIG. 13, the output voltage (the second voltage V2) of the second regulator 62 may not exceed the second limit voltage V2_limit=2.8 V.

Accordingly, if the output voltage (the second voltage V2) of the second regulator 62 does not exceed the second limit voltage V2_limit (2.8 V), the second voltage error signal V2err may not be outputted from the second voltage comparison circuit 122a. Therefore, the abnormal state may be difficult to detect regardless of the short circuit having occurred between the respective live wires of the first power supply line 81 and the second power supply line 82.

<Functions and Effects of Power Calculation Circuit and Power Comparison Circuit>

The endoscope according to the present embodiment is provided with the power calculation circuit, the power comparison circuit, and the like, as described above, and enables control of the processor power supply unit 33 by calculating not only an output voltage and an output current (input current) but also an output power related to the regulator that has been supplied with power from the processor power supply unit 33, comparing the calculated output power with predetermined comparison data (limit power value data), detecting an abnormality in the power supply line by power measurement, to cope with a novel situation.

As described above, the first power calculation circuit 101 in the present embodiment calculates the product of the value of the output voltage V1 of the first regulator 61 and the value of the input current (output current) I1 of the first regulator 61 via the AD converter, that is, the value of the first power P1 of the first regulator output Vol1.

Note that although the second power calculation circuit 102 and the third power calculation circuit 103 respectively have similar components and functions and effects to the above-described first power calculation circuit 101, the first power calculation circuit 101 will be described as a representative.

As described above, the first power comparison circuit 121c compares the first power P1 to be outputted from the first power calculation circuit 101 with the predetermined first power comparison data P1ref (i.e., the first limit power P1_limit), and outputs the error signal first power error signal P1err when the first power P1 exceeds the first limit power P1_limit.

Note that although the second power comparison circuit 122c and the third power comparison circuit 123c also have similar components and functions and effects to the components and the functions and effect of the first power comparison circuit 121c, the first power comparison circuit 121c will be described as a representative.

<Function of Power Comparison Circuit when Short Circuit has Occurred Between First Power Supply Line 81 and Second Power Supply Line 82>

As described above, the respective functions and effects of the first power calculation circuit 101 and the first power comparison circuit 121c obtained when a short circuit or a state close to the short circuit has occurred between the respective live wire sides of the first power supply line 81 (the analog power supply line; a rated voltage of 3 V and a rated current of 10 mA) and the second power supply line 82 (the interface power supply line; a rated voltage of 2 V and a rated current of 2 mA) will be described.

At this time, the potential difference between both the power supply lines is small, and the degree of change in current is small. Therefore, in the first voltage comparison circuit 121a and the first current comparison circuit 121b, an abnormality (a short circuit) in each of the power supply lines may be difficult to detect, as described above.

On the other hand, in the present embodiment, the abnormality (due to the short circuit or the like) in the first power supply line 81 can be detected by comparing the first power P1 as a power of the first regulator output Vol1 calculated in the first power calculation circuit 101 with the predetermined first power comparison data P1ref (i.e., the first limit power P1_limit) in the first power comparison circuit 121c.

FIG. 14 is a diagram illustrating a relationship between the first power P1 related to the first power supply line 81 and the first limit power P1_limit (=the first power comparison data P1ref) when a short circuit has occurred between the live wire side of the first power supply line 81 and the live wire side of the second power supply line 82 in the endoscope according to the present embodiment.

Note that in the present embodiment, the first limit power P1_limit (=the first power comparison data P1ref) is set to a value corresponding to a power value obtained when it is assumed that a short circuit has occurred between the live wire side of the first power supply line 81 and the live wire side of the second power supply line 82, as described above.

As illustrated in FIG. 14, when a short circuit or a state close to the short circuit has occurred between the respective live wire sides of the first power supply line 81 (the analog power supply line; a rated voltage of 3 V and a rated current of 10 mA) and the second power supply line 82 (the interface power supply line; a rated voltage of 2 V and a rated current of 2 mA), the first power P1 related to the first power supply line 81 (i.e., the first power P1 as a power of the first regulator output Vol1 calculated in the first power calculation circuit 101) can conceivably increase to exceed the above-described first limit power P1_limit (=the first power comparison data P1ref).

At this time, the first power comparison circuit 121c compares the inputted first power P1 with the first limit power P1_limit (=the first power comparison data P1ref), and outputs the error signal first power error signal P1err when the value of the first power P1 exceeds the first limit power P1_limit (step S15 in FIG. 6).

The OR circuit 130 outputs, when it receives the error signal first power error signal P1err, the error signal ERROR toward the power supply control unit 27, assuming that a malfunction such as a short circuit has occurred in the first power supply line 81 (step S41 in FIG. 6).

Then, the power supply control unit 27 transmits, when it receives the error signal ERROR from the OR circuit 130, a control signal to the processor power supply unit 33 in the video processor 3, and stops supplying power to each of the regulators (the first regulator 61, the second regulator 62, and the third regulator 63) from the processor power supply unit 33 (step S42).

As described above, the endoscope according to the first embodiment enables, even when the current value and the voltage value to be outputted from the regulator do not respectively exceed the limit values in cases such as a case where an abnormality in the power supply line configured to supply power to the image pickup device, particularly a short circuit has occurred between the respective live wires of the plurality of power supply lines in close proximity to each other, an abnormal state to be accurately detected even when the short circuit or the like has occurred between the respective live wires of the power supply lines by calculating the power value of each of the power supply lines and comparing the calculated power value with a predetermined limit value (e.g., a power value obtained when it is assumed that a short circuit has occurred between the respective live wires of the power supply lines in close proximity to each other).

In the above-described embodiment, the image pickup device requiring the three power supplies (regulators) is assumed, is provided with the current detecting function, the voltage detecting function, and the power detecting function for each of the power supply lines, and is configured to stop supplying power to the image pickup device when an abnormality has been detected in any one of the detecting functions.

In the present embodiment, the power detecting function is further added to prevent unreliable detection associated with detection of an abnormality in each of the power supply lines by only conventional current detection. For example, an image pickup device requiring two power supplies is provided with a current detecting function and a voltage detecting function for at least one power supply line and is configured to perform power detection (a product of current detection and voltage detection) in addition to overcurrent detection and stop supplying power to the image pickup device if an abnormality has occurred in either one of the detecting functions.

Note that although examples of the power supply line wired within the cable 23 include the first power supply line 81, the second power supply line 82, and the third power supply line 83 in the present embodiment, the power supply line is not limited to the power supply lines. Further, the effect of the present invention is also applicable to an example in which a plurality of power supply lines are disposed.

Although examples of the short circuit between the respective live wires of the power supply lines in close proximity to each other include the short circuit between the first power supply line 81 and the second power supply line 82 in the present embodiment, it is apparent that the present invention is not limited to these examples. A short circuit between other power supply lines can also be accurately detected by the above-described configuration.

Note that the configuration in which an abnormality in each of the power supply lines can be detected using hardware (the FPGA) is disclosed in the above-described embodiment, the configuration according to the present embodiment can be replaced with another hardware circuit, for example, a microcontroller including an AD converter and a comparison circuit.

Figure 18:
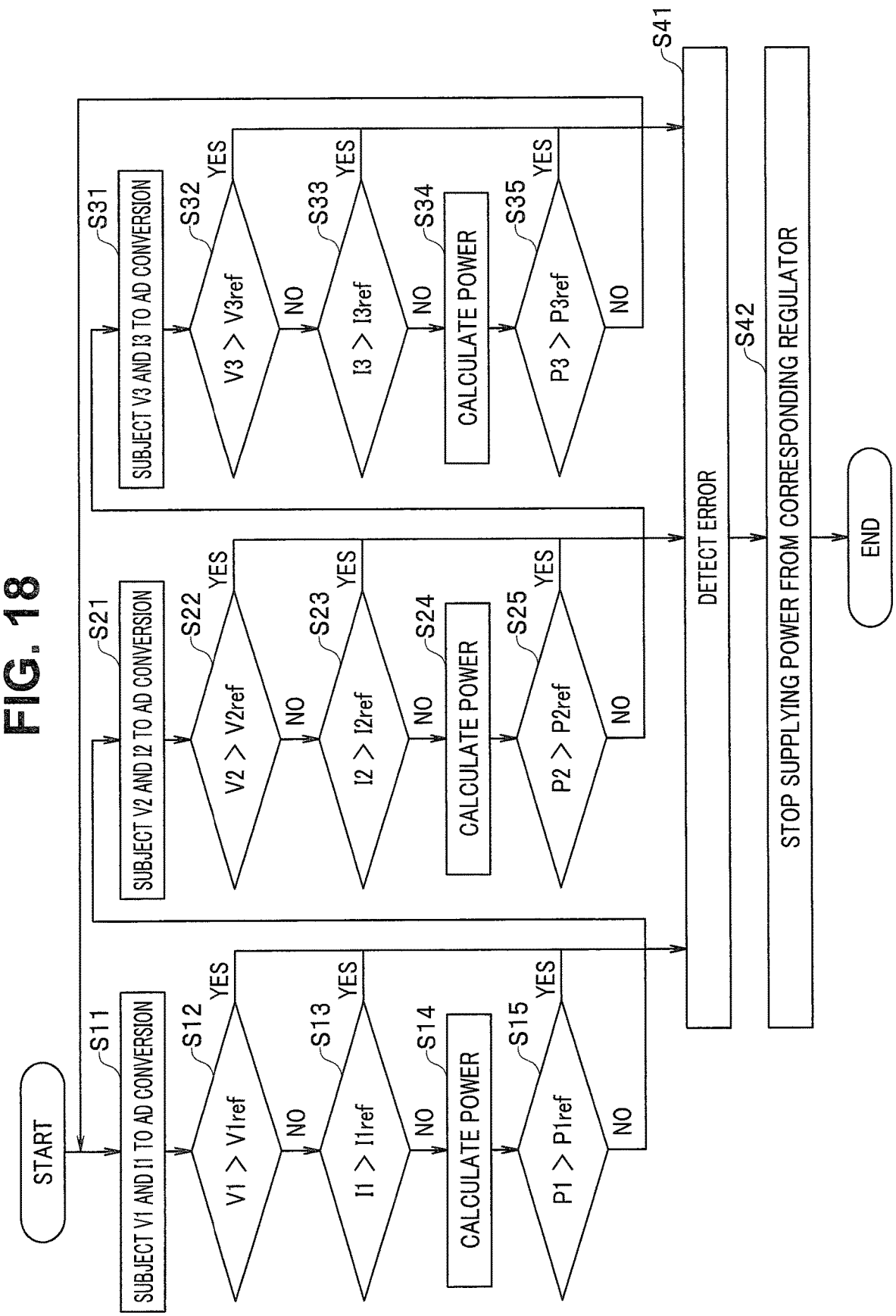
FIG. 18 is a flowchart illustrating an error detecting function associated with a regulator output voltage, an output current, and power consumption related to each power supply line in the endoscope according to the second embodiment.

An operation of the above-described microcontroller (program) conforms to a flowchart illustrated in FIG. 18. The flowchart illustrated in FIG. 18 discloses a method according to the present invention. In addition, the program related to the microcontroller and further a medium storing the program are also included in the present invention. On the other hand, a configuration in which the microcontroller and another hardware (e.g., an FPGA) are combined with each other is also included in the present invention.

Although the configuration of the endoscope system including the endoscope has been cited as an example of the embodiment of the present invention, the present invention is not limited to the example. The present invention is also applicable to another image pickup system having an image processing function.

Further, the present invention is not limited to the above-described embodiment, but various changes, modifications, and the like are possible without departing from the scope and spirit of the invention. For example, some of components in the embodiment are also intended to be included in the present invention.

Second Embodiment

Then, a second embodiment of the present invention will be described.

Although the above-described endoscope according to the first embodiment controls supply of power from the processor power supply unit 33 (configured to supply power to the first regulator 61, the second regulator 62, and the third regulator 63) in the video processor 3 from the side of the endoscope 2 when an abnormality has occurred in each of the power supply lines (see FIG. 2), an endoscope according to the second embodiment has a similar basic configuration to the basic configuration of the first embodiment while controlling an operation of each regulator itself within the endoscope 2 when an abnormality has occurred in the power supply line.

Therefore, only a difference from the first embodiment is described, and description of common portions is omitted.

Figure 15:
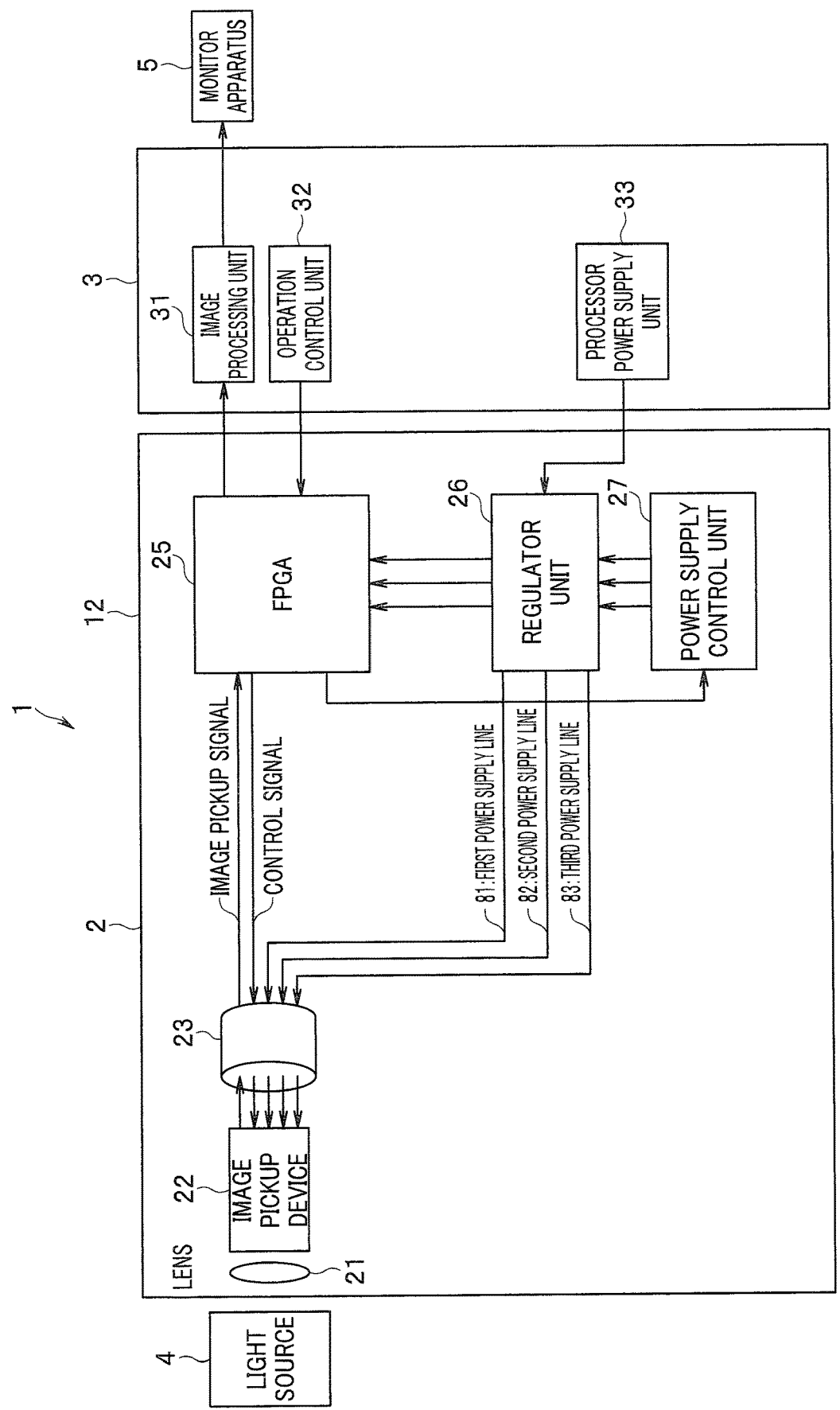
FIG. 15 is a block diagram illustrating an electrical configuration of an endoscope system including an endoscope according to a second embodiment of the present invention.
Figure 16:
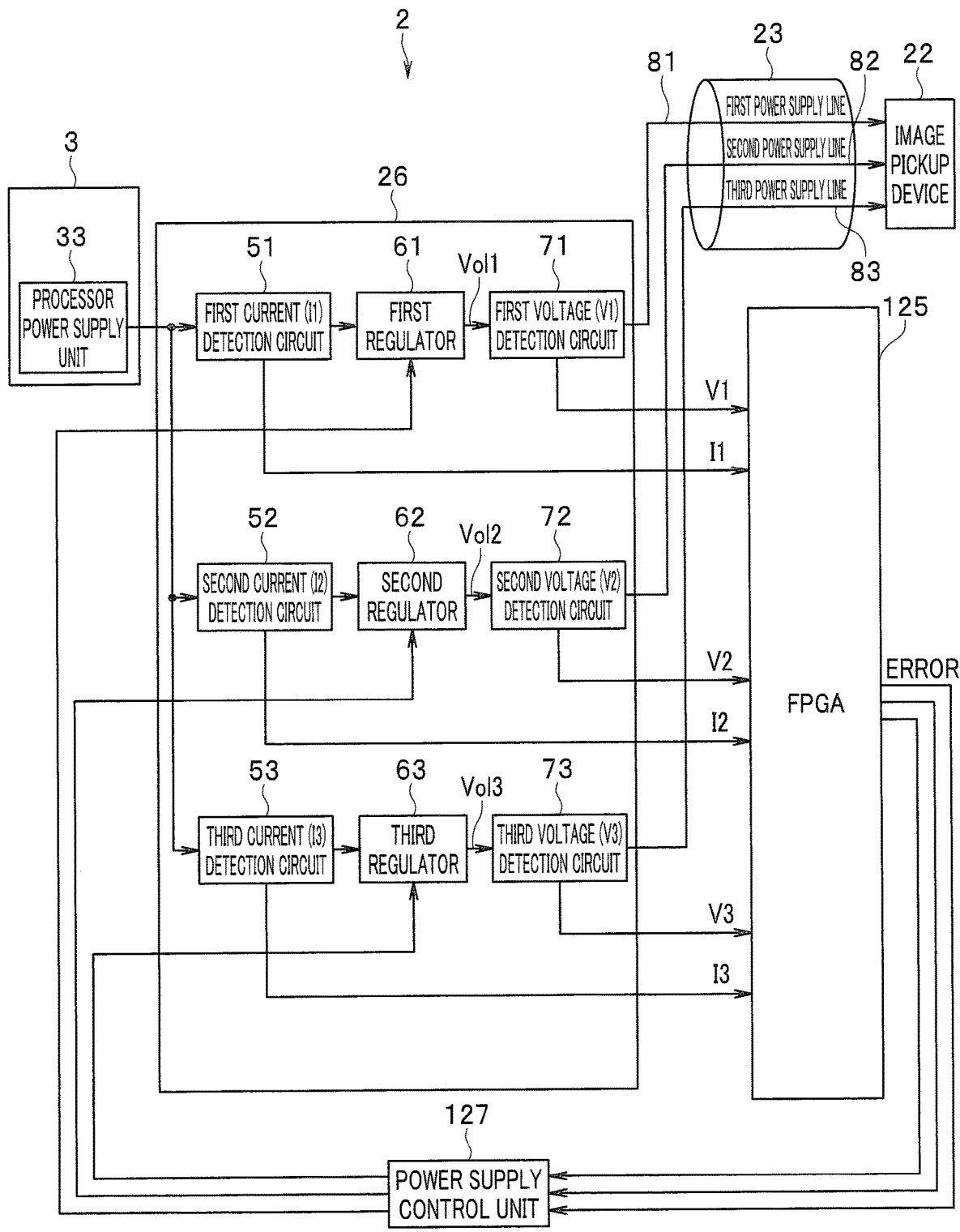
FIG. 16 is a block diagram illustrating a configuration of an FPGA, a regulator unit, a power supply control unit, and a peripheral portion in the endoscope according to the second embodiment.
Figure 17:
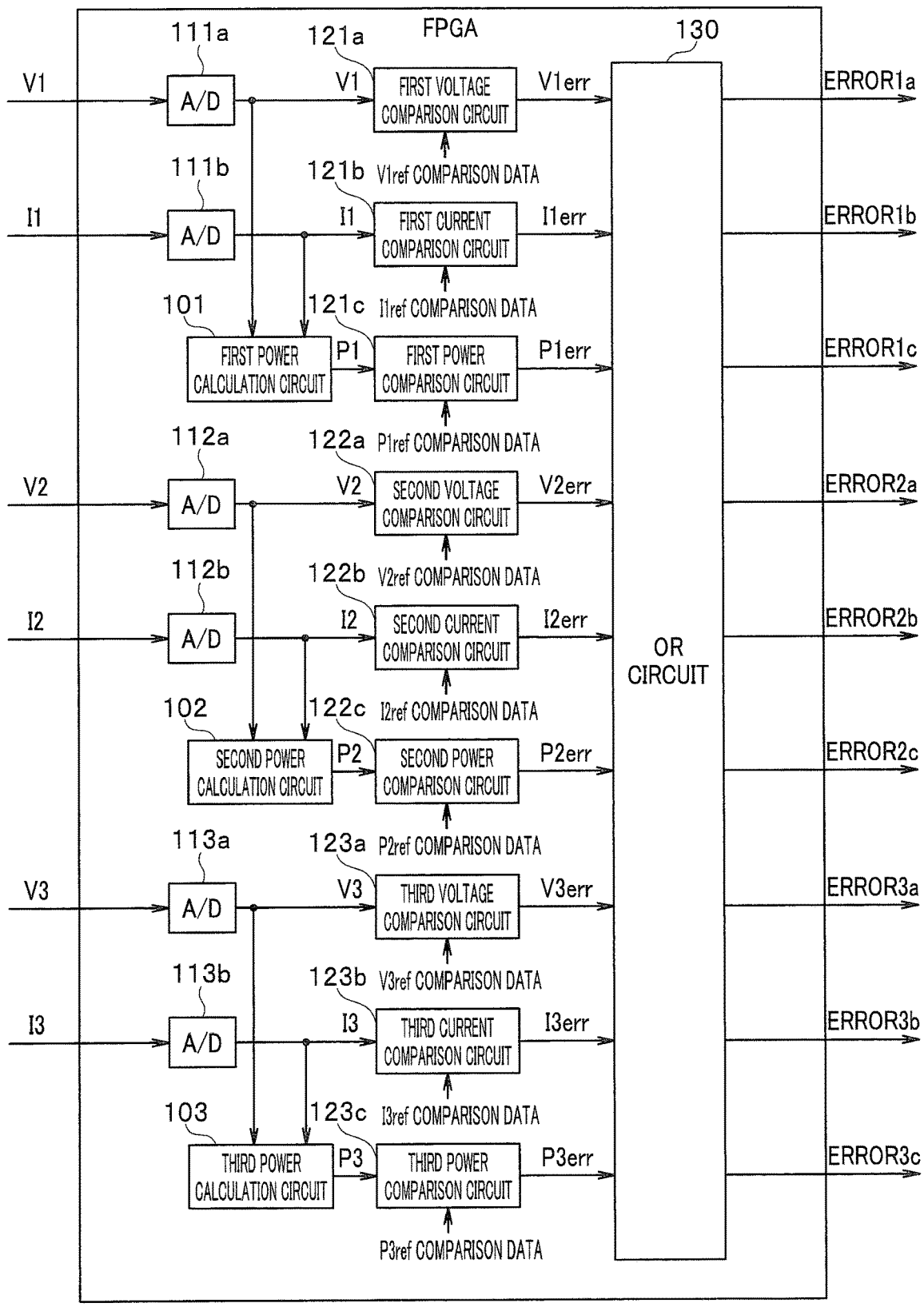
FIG. 17 is a block diagram illustrating a configuration within the FPGA in the endoscope according to the second embodiment.

FIG. 15 is a block diagram illustrating an electrical configuration of an endoscope system including the endoscope according to the second embodiment of the present invention, and FIG. 16 is a block diagram illustrating a configuration of an FPGA, a regulator unit, a power supply control unit, and a peripheral portion in the endoscope according to the second embodiment. FIG. 17 is a block diagram illustrating a configuration within the FPGA in the endoscope according to the second embodiment, and FIG. 18 is a flowchart illustrating respective error detecting functions associated with a regulator output voltage, an output current, and power consumption related to each of power supply lines in the endoscope according to the second embodiment.

In the above-described endoscope 2 according to the first embodiment, the OR circuit 130 in the FPGA 25 outputs the error signal ERROR when it has received any one of the individual error signals (the first voltage error signal V1err to the third voltage error signal V3err, the first current error signal I1err to the third current error signal I3 err, and the first power error signal P1err to the third power error signal P3err), respectively, from each of the comparison circuits (the first voltage comparison circuit 121a to the third voltage comparison circuit 123a, the first current comparison circuit 121b to the third current comparison circuit 123b, and the first power comparison circuit 121c to the third power comparison circuit 123c) in the FPGA 25 (see step S41 illustrated in FIGS. 4 and 6).

In the first embodiment, the power supply control unit 27 controls the processor power supply unit 33 in the video processor 3 when it receives the error signal ERROR from the FPGA 25, and performs control to stop supplying respective powers to the first regulator 61, the second regulator 62, and the third regulator 63 (see step S42 illustrated in FIGS. 3 and 6).

On the other hand, in the endoscope according to the second embodiment, an OR circuit 130 in an FPGA 125 transmits, when it has received individual error signals (a first voltage error signal V1err, a first current error signal I1err, a first power error signal P1err, a second voltage error signal V2err, a second current error signal I2err, a second power error signal P2err, a third voltage error signal V3err, a third current error signal I3err, and a third power error signal P3err), respectively, from comparison circuits, described above, error signals (ERROR 1a, ERROR 1b, ERROR 1c, ERROR 2a, ERROR 2b, ERROR 2c, ERROR 3a, ERROR 3b, and ERROR 3c) respectively corresponding to the individual error signals toward a power supply control unit 127, as illustrated in FIG. 17.

The power supply control unit 127 in the second embodiment performs control (e.g., off control) of an operation of a corresponding regulator (a first regulator 61, a second regulator 62, or a third regulator 63) in response to the error signal from the FPGA 125, as illustrated in FIGS. 16 and 15 (FIG. 18, step S142).

Note that although the power supply control unit 127 controls the operation of the corresponding regulator in response to the error signal from the FPGA 125 in the second embodiment, the power supply control unit 127 may control supply of power from a processor power supply unit 33 in a video processor 3 in addition to controlling the regulator.

As described above, the endoscope according to the second embodiment controls the operation of the corresponding regulator itself when there has occurred an abnormality in each of the power supply lines configured to supply power to an image pickup device, particularly a short circuit between respective live wires of the plurality of power supply lines in close proximity to each other, for example. Therefore, an abnormal state can also be more accurately detected when a short circuit or the like has occurred between the respective live wires of the power supply lines.

Third Embodiment

Then, a third embodiment of the present invention will be described.

An endoscope according to the third embodiment forms the function of the above-described power supply control unit 27 within the FPGA 25 in the first embodiment. Since other components are similar to the components of the first embodiment, only a difference from the first embodiment is described, and description of common portions is omitted.

Figure 19:
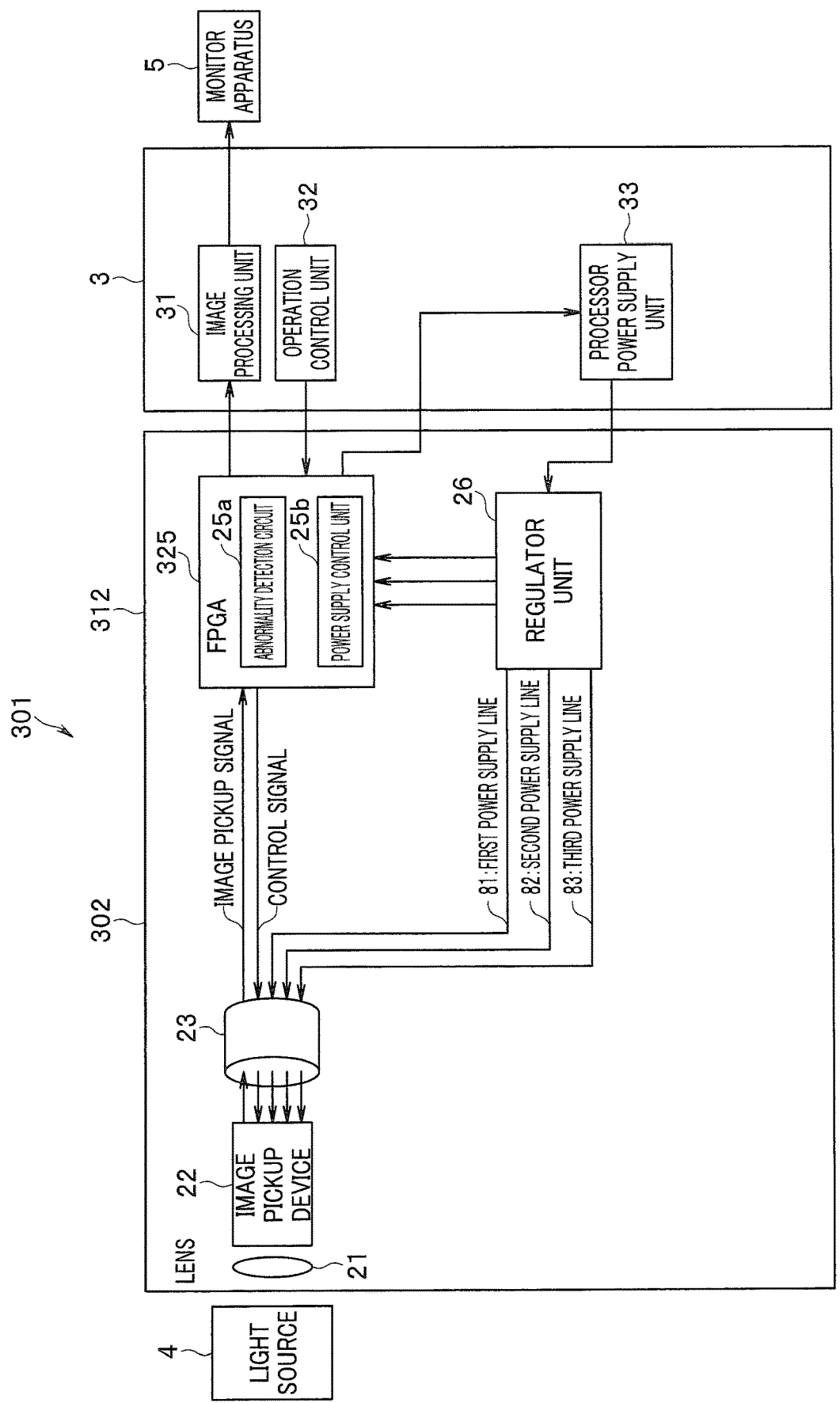
FIG. 19 is a block diagram illustrating an electrical configuration of an endoscope system including an endoscope according to a third embodiment of the present invention.
Figure 20:
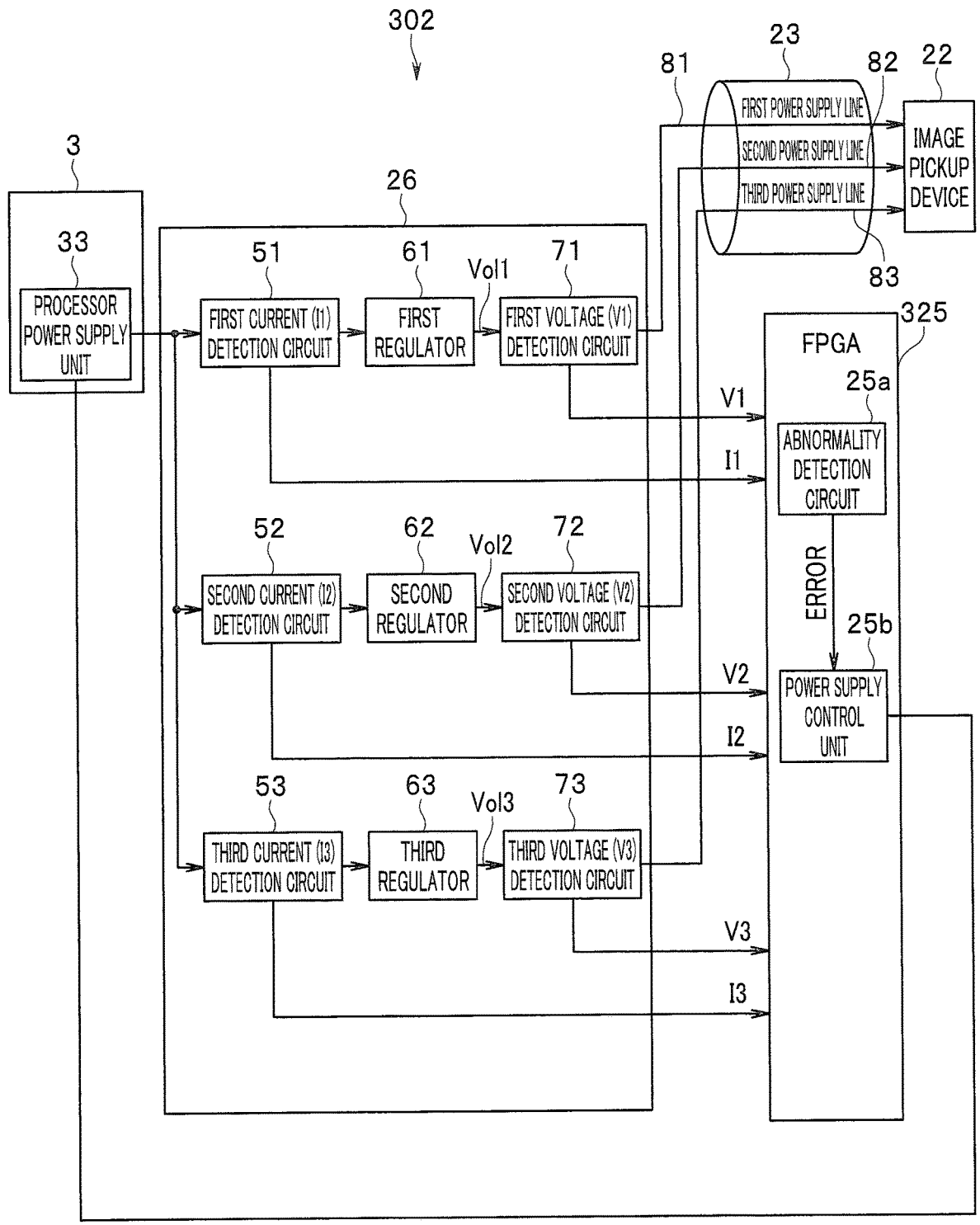
FIG. 20 is a block diagram illustrating a configuration of an FPGA, a regulator unit, and a peripheral portion in the endoscope according to the third embodiment.
Figure 21:
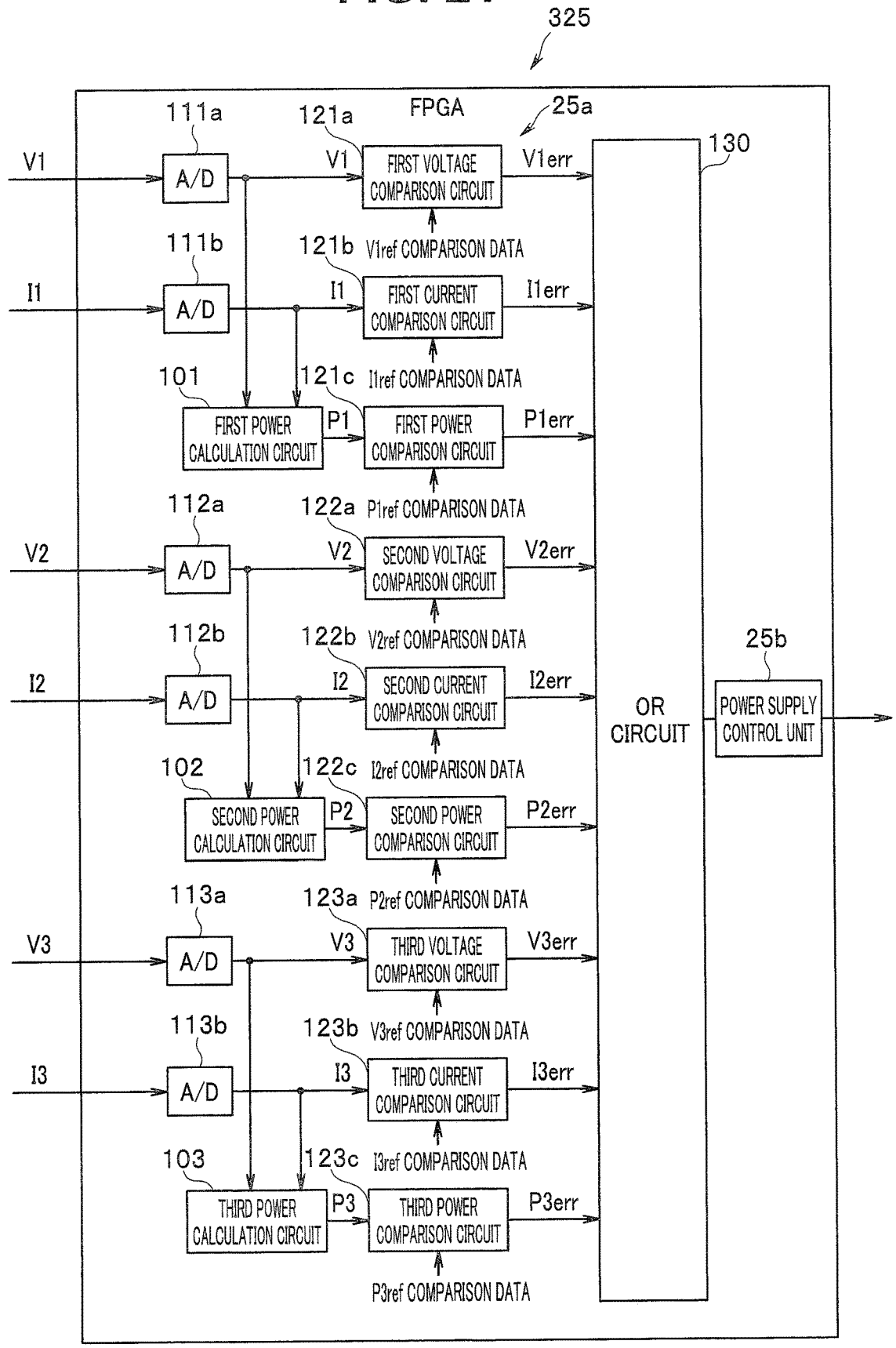
FIG. 21 is a block diagram illustrating a configuration within the FPGA in the endoscope according to the third embodiment.

FIG. 19 is a block diagram illustrating an electrical configuration of an endoscope system including the endoscope according to the third embodiment of the present invention, and FIG. 20 is a block diagram illustrating a configuration of an FPGA, a regulator unit, and a peripheral portion in the endoscope according to the third embodiment. FIG. 21 is a block diagram illustrating a configuration within the FPGA in the endoscope according to the third embodiment.

As illustrated in FIGS. 19 to 21, a similar function to the function of the FPGA 25 in the first embodiment, that is, an FPGA (field programmable gate array) 325 in which various types of comparison circuits and the like configured to judge an abnormality in each of power supply lines are formed is disposed in a connector 312 in an endoscope 302 according to the third embodiment.

In the third embodiment, in the FPGA 325, an abnormality detection circuit 25a having respective functions of the above-described various types of comparison circuits configured to judge an abnormality in each of the power supply lines is formed while a power supply control unit 25b configured to exhibit a similar function to the function of the above-described power supply control unit 27 in the first embodiment is formed.

The abnormality detection circuit 25a in the FPGA 325 is formed as a circuit configured to exhibit a similar function to respective functions of various types of comparison circuits (a first voltage comparison circuit 121a to a third power comparison circuit 123c) configured to judge an abnormality in each of the power supply lines (a first power supply line 81, a second power supply line 82, and a third power supply line 83), as described above, and transmits an error signal ERROR to the power supply control unit 25b in the FPGA 325 when the abnormality has occurred in the power supply line.

The power supply control unit 25b in the FPGA 325 receives the error signal ERROR from the abnormality detection circuit 25a in the FPGA 325, like the power supply control unit 27 in the first embodiment while transmitting a control signal for controlling (e.g., turning on and off) a processor power supply unit 33 in a video processor 3 toward the video processor 3 in response to the error signal ERROR.

As described above, the endoscope according to the third embodiment enables an abnormal state to be accurately detected when there has occurred an abnormality in each of the power supply lines configured to supply power to an image pickup device, particularly a short circuit between respective live wires of the plurality of power supply lines in close proximity to each other, like in the first embodiment.

Fourth Embodiment

Then, a fourth embodiment of the present invention will be described.

An endoscope according to the fourth embodiment does not include the "voltage comparison circuits" such as the first voltage comparison circuit 121a, the second voltage comparison circuit 122a, and the third voltage comparison circuit 123a but includes only the "current comparison circuits" and the "power comparison circuits" and detects an abnormality in each of the power supply lines by "the current comparison circuits: the first current comparison circuit 121b, the second current comparison circuit 122b, and the third current comparison circuit 123b" and "the power comparison circuits: the first power comparison circuit 121c, the second power comparison circuit 122c, and the third power comparison circuit 123c" within the FPGA 25 in the first embodiment.

Since other components are similar to the components of the first embodiment, only a difference from the first embodiment is described, and description of common portions is omitted.

Figure 22:
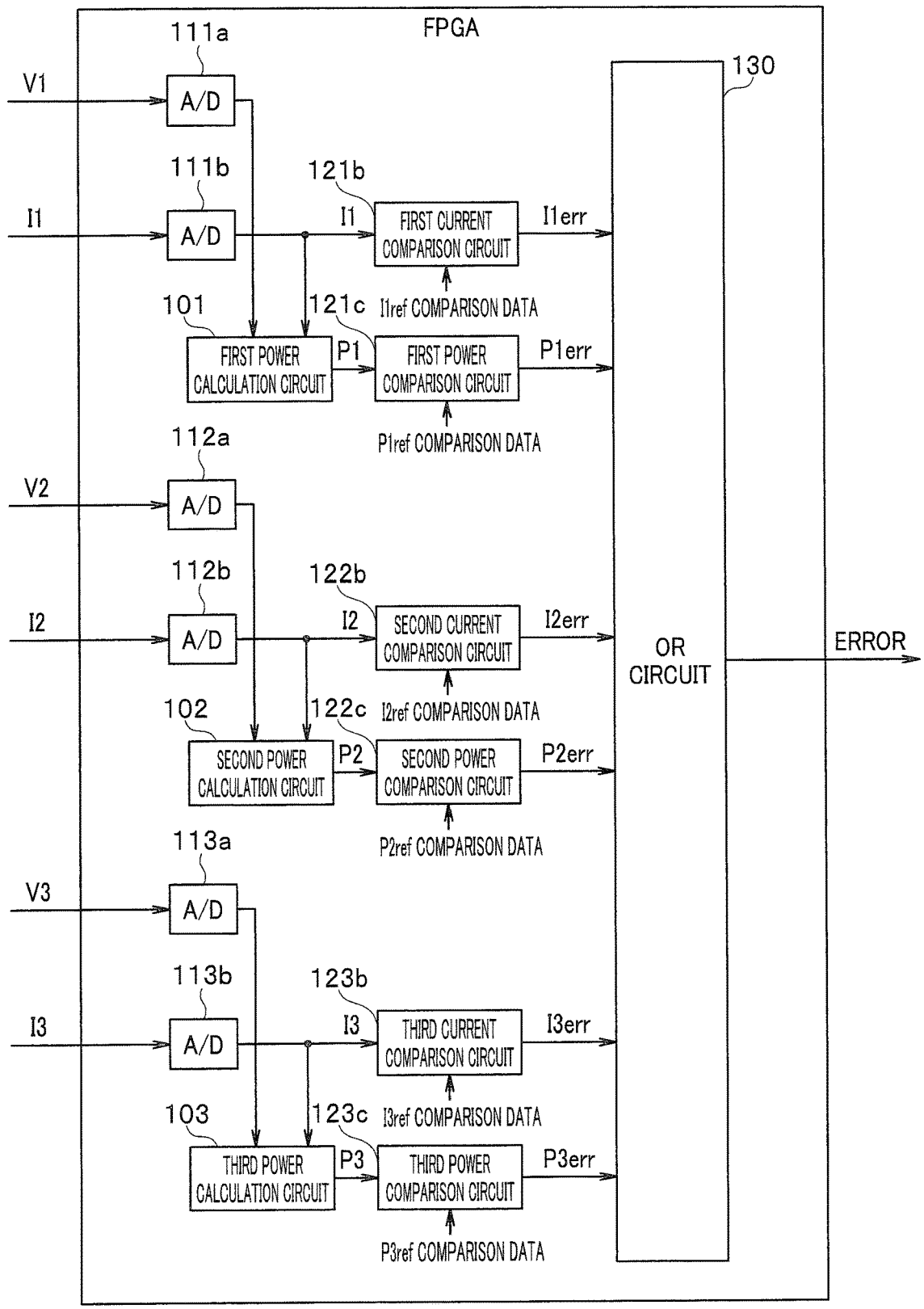
FIG. 22 is a block diagram illustrating a configuration within an FPGA in an endoscope according to a fourth embodiment of the present invention.

FIG. 22 is a block diagram illustrating a configuration within an FPGA in the endoscope according to the fourth embodiment of the present invention.

As illustrated in FIG. 22, an FPGA 425 in the fourth embodiment includes a first current comparison circuit 121b, a second current comparison circuit 122b, and a third current comparison circuit 123b configured to respectively exhibit similar functions to the functions of the "current comparison circuits" and a first power comparison circuit 121c, a second power comparison circuit 122c, and a third power comparison circuit 123c configured to respectively exhibit similar functions to the functions of the "power comparison circuits" formed within the FPGA 25 in the first embodiment as a comparison circuit configured to detect an abnormality in each of power supply lines (a first power supply line 81, a second power supply line 82, and a third power supply line 83).

The "current comparison circuits" and the "power comparison circuits" in the fourth embodiment respectively produce similar functions and effects to the functions and effects of the "current comparison circuits" and the "power comparison circuits" in the first embodiment, and hence detailed description is omitted.

As described above, the endoscope according to the fourth embodiment does not include "voltage comparison circuits" but includes only the "current comparison circuits" and the "power comparison circuits", unlike in the above-described first embodiment. Therefore, a circuit configuration can be simplified while an abnormal state can be accurately detected when there has occurred an abnormality in each of the power supply lines configured to supply power to an image pickup device, particularly a short circuit between respective live wires of the plurality of power supply lines in close proximity to each other, like in the first embodiment.

Fifth Embodiment

Then, a fifth embodiment of the present invention will be described.

An endoscope according to the fifth embodiment does not include the "power comparison circuits" such as the first power comparison circuit 121c, the second power comparison circuit 122c, and the third power comparison circuit 123c but includes only the "current comparison circuits" and the "voltage comparison circuits" and detects an abnormality in each of the power supply lines by the "current comparison circuits: the first current comparison circuit 121b, the second current comparison circuit 122b, and the third current comparison circuit 123b" and the "voltage comparison circuits: the first voltage comparison circuit 121a, the second voltage comparison circuit 122a, and the third voltage comparison circuit 123a" within the FPGA 25 in the first embodiment.

Since other components are similar to the components of the first embodiment, only a difference from the first embodiment is described, and description of common portions is omitted.

Figure 23:
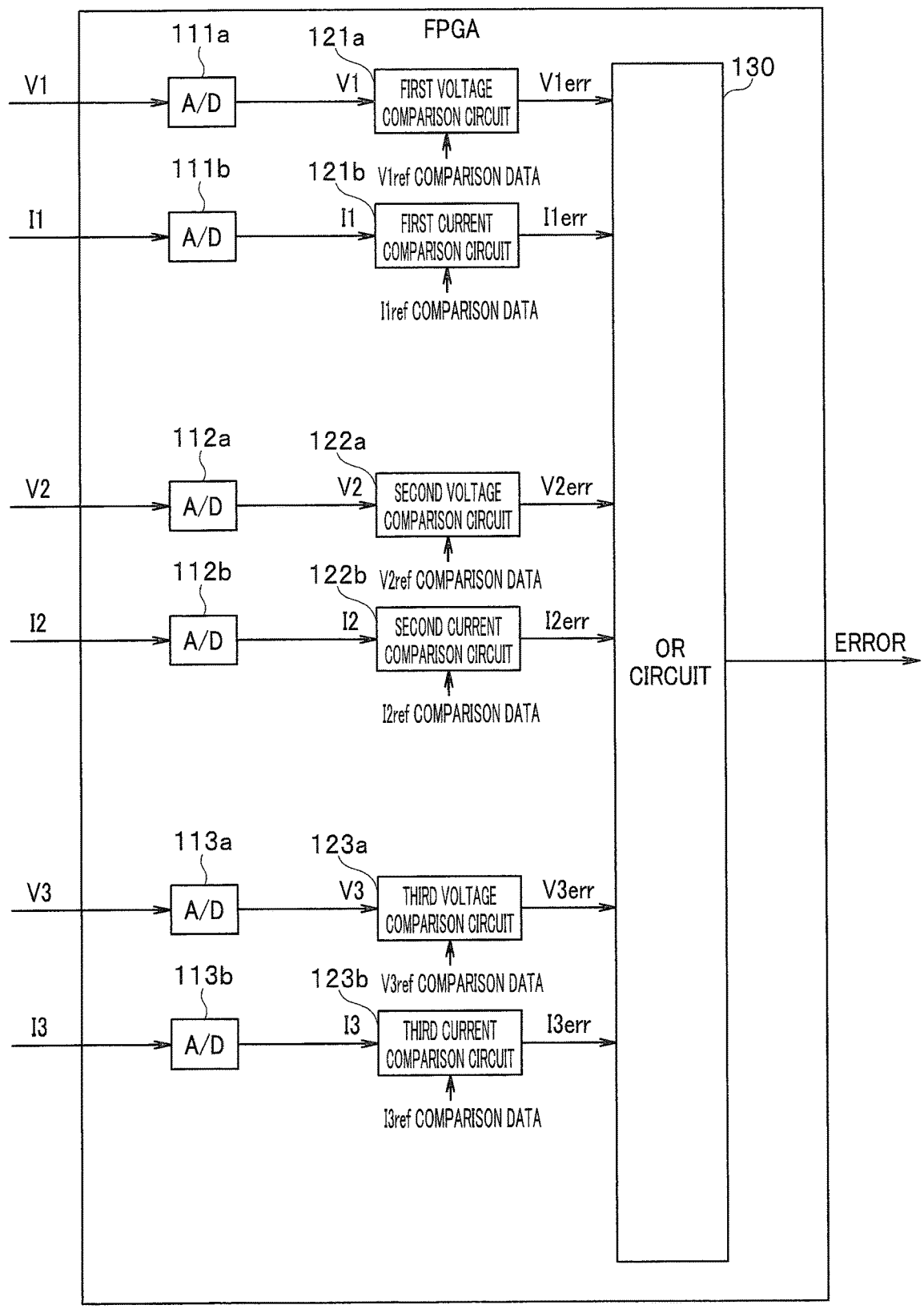
FIG. 23 is a block diagram illustrating a configuration within an FPGA in an endoscope according to a fifth embodiment of the present invention.

FIG. 23 is a block diagram illustrating a configuration within an FPGA in the endoscope according to the fifth embodiment of the present invention.

As illustrated in FIG. 23, an FPGA 525 in the fifth embodiment includes a first current comparison circuit 121b, a second current comparison circuit 122b, and a third current comparison circuit 123b configured to respectively exhibit similar functions to the functions of the "current comparison circuits" and a first voltage comparison circuit 121a, a second voltage comparison circuit 122a, and a third voltage comparison circuit 123a configured to respectively exhibit similar functions to the functions of the "voltage comparison circuits" formed within the FPGA 25 in the first embodiment as a comparison circuit configured to detect an abnormality in each of power supply lines (a first power supply line 81, a second power supply line 82, and a third power supply line 83).

Note that the FPGA 525 does not include the power comparison circuits in the first embodiment. Therefore, the first power calculation circuit 101, the second power calculation circuit 102, and the third power calculation circuit 103 formed in the FPGA 25 in the first embodiment are also omitted.

The "current comparison circuits" and the "voltage comparison circuits" in the fifth embodiment respectively produce similar functions and effects to the functions and effects of the "current comparison circuits" and the "voltage comparison circuits" in the first embodiment, and hence detailed description is omitted.

As described above, the endoscope according to the fifth embodiment does not include "power comparison circuits" and "power calculation circuits" but includes only the "current comparison circuits" and the "voltage comparison circuits", unlike in the above-described first embodiment. Therefore, a circuit configuration can be simplified while an abnormal state can be accurately detected when there has occurred an abnormality in each of the power supply lines configured to supply power to an image pickup device, particularly a short circuit between respective live wires of the plurality of power supply lines in close proximity to each other, like in the first embodiment.

FIG. 24 is a block diagram illustrating a configuration within an FPGA in an endoscope system including a stereoscopic endoscope.

An endoscope system 601 including a stereoscopic endoscope 602 includes the stereoscopic endoscope 602 and a video processor 603.

The stereoscopic endoscope 602 includes a CCD for left eye 621a and a CCD for right eye 621b each provided in a distal end portion of an insertion section. The CCD for left eye 621a and the CCD for right eye 621b are connected to a scope substrate 630 disposed in a connector section 612 via a cable 622.

The scope substrate 630 includes an AFE 623a configured to convert an analog image pickup signal to be outputted from the CCD for left eye 621a into a digital signal and output the digital signal, a DSP 624a configured to subject the outputted digital signal from the AFE 623a to predetermined DSP processing, an AFE 623b configured to convert an analog image pickup signal to be outputted from the CCD for right eye 621b into a digital signal and output the digital signal, and a DSP 624b configured to subject the outputted digital signal from the AFE 623b to predetermined DSP processing.

The scope substrate 630 includes a CCD power supply 635 configured to drive the CCD for left eye 621a and the CCD for right eye 621b, an overcurrent detection circuit 627 configured to detect an overcurrent of a power supply current to be outputted from the CCD power supply 635, and a power supply for detection circuit 626 as a power supply configured to operate the overcurrent detection circuit 627.

The overcurrent detection circuit 627 monitors the above-described CCD power supply 635, and detects an overcurrent occurring when one or both of the CCD for left eye 621a and the CCD for right eye 621b enters or enter an abnormal state such as a short circuit.

On the other hand, an FPGA 625 is disposed in the scope substrate 630. The FPGA 625 includes a CCD signal processing unit 631 configured to receive respective output signals of the DSP 624a and DSP 624b, subject the output signals to predetermined signal processing, and then output the output signals toward the video processor 603, and a driving signal generation unit 632 configured to generate various types of driving signals for controlling driving of the CCD for left eye 621a and the CCD for right eye 621b upon receiving a predetermined control signal from the video processor 603.

Further, the scope substrate 630 includes a driving signal control unit 633 configured to control generation of all control signals for endoscope control including the driving signals to be generated in the driving signal generation unit 632, and a power supply control unit 634 configured to control all power supplies including the CCD power supply 635.

The driving signal control unit 633 controls each of circuits to stop controlling all signals including the driving signals in the driving signal generation unit 632 upon receiving overcurrent detection information from the overcurrent detection circuit 627.

The power supply control unit 634 performs control to stop supplying respective powers from all the power supplies including the CCD power supply 635 upon receiving the overcurrent detection information from the overcurrent detection circuit 627.

The present invention is not limited to the above-described embodiments, but various changes, modifications, and the like are possible without departing from the scope and spirit of the invention.

What is claimed is:

1. An image pickup apparatus comprising: an image pickup device; a first power supply line configured to transmit a first voltage to the image pickup device; a second power supply line arranged adjacent to the first power supply line and configured to transmit a second voltage different from the first voltage to the image pickup device; a first regulator configured to generate the first voltage from a power supply output generated in a predetermined power supply and output the first voltage to the first power supply line; a second regulator configured to generate the second voltage from the power supply output and output the second voltage to the second power supply line; a first current detection circuit configured to detect a first current inputted to an input terminal of the first regulator; a first voltage detection circuit configured to detect the first voltage related to a first regulator output outputted from an output terminal of the first regulator; a first power calculation circuit configured to calculate a first power value as a product of a value of the first current detected in the first current detection circuit and a value of the first voltage detected in the first voltage detection circuit; a power supply line abnormality judgment circuit configured to judge an abnormal state related to the first power supply line based on at least the first power value calculated in the first power calculation circuit; and a power supply control circuit configured to control an output of the power supply based on a judgment result in the power supply line abnormality judgment circuit;
   wherein the power supply line abnormality judgment circuit compares the first power value calculated in the first power calculation circuit with a value corresponding to a power value obtained when it is assumed that a short circuit occurs between the first power supply line and the second power supply line in a state in which the first voltage is supplied to the first power supply line and the second voltage is supplied to the second power supply line, and judges an abnormal state related to the first power supply line.

* * * * *